(12) United States Patent
Herzenberg et al.

US008731844B2

(10) Patent No.: US 8,731,844 B2
(45) Date of Patent: May 20, 2014

(54) SYSTEM AND METHOD FOR SELECTING A MULTIPARAMETER REAGENT COMBINATION AND FOR AUTOMATED FLUORESCENCE COMPENSATION

(76) Inventors: Leonore A. Herzenberg, Stanford, CA (US); David Rhodes Parks, San Francisco, CA (US); Stephen Meehan, Burnaby (CA); Wayne A. Moore, San Francisco, CA (US)

( * ) Notice: Subject to any disclaimer, the term of this patent is extended or adjusted under 35 U.S.C. 154(b) by 162 days.

(21) Appl. No.: 13/105,570

(22) Filed: May 11, 2011

(65) Prior Publication Data

US 2011/0282870 A1 Nov. 17, 2011

Related U.S. Application Data

(63) Continuation-in-part of application No. 12/467,662, filed on May 18, 2009.

(60) Provisional application No. 61/333,381, filed on May 11, 2010, provisional application No. 61/466,836, filed on Mar. 23, 2011, provisional application No. 61/053,974, filed on May 16, 2008.

(51) Int. Cl.
 *G01N 33/48* (2006.01)
 *G01N 33/50* (2006.01)
 *G01N 31/00* (2006.01)

(52) U.S. Cl.
 USPC .................................. 702/19; 702/21; 702/22

(58) Field of Classification Search
 None
 See application file for complete search history.

*Primary Examiner* — Eric S DeJong
(74) *Attorney, Agent, or Firm* — Beverly W. Lubit; Greenberg Traurig, LLP

(57) ABSTRACT

The invention provides a system and method for selecting an optimal multimarker reagent combination for the identification and/or quantification of molecules in or on cells with or without reference to fluorescence or other properties of at least one fluorescent dye or other instrument-measurable atom or molecule associated directly or indirectly with the reagent combination. The method includes specifying, using a computer, a plurality of markers to be detected by a plurality of reagents, generating, using a computer, a plurality of reagent combinations comprising the plurality of reagents to detect the plurality of markers, wherein the reagent combinations are ranked according to at least one user-defined or system-defined criterion, and selecting the optimal reagent combination or providing a rank-ordered list of combinations.

46 Claims, 18 Drawing Sheets

FIG. 4

| | See more | SKU |
|---|---|---|
| root | | |
| ☐ Antibody | Table (remove tree)  F8 | 202 |
| ☐ Anti-Ig | Recent trees  ▷ | 203 |
| ☐ Handle-detector | Manage view  ▷ | 204 |
| ☐ Non antibody | 🔍 Find  F3 | |
| | Hide search node panel | 202 |
| | All levels at startup | 122 |
| | 👓 Find again  Ctrl+X | 111 |
| | ✓ Require ctrl key to select multiples discontiguously | 117 |
| | 👓 | V35118 |

Show reagents for

FIG. 5

| Find/filter Reagent lot(s) | | |
|---|---|---|
| Column name | Operator | Search value |
| See more | | |
| SKU | | |
| Epitope | | |
| Color/handle | not starts with ◁ | *flourescein (FITC)* |
| Product name | ends with | |
| Antibody clone | not ends with | |
| Ab source species | starts with | |
| IgH Isotype | not starts with | |
| IgL Isotype | > | a operator to filter on |
| Species detected | >= | |
| Known NON reactivities | < | |
| Received ul | <= ▷ | |

Viewing 0 of 47 Reagent lot(s)   ⎕ Remove filter | ⧉ Apply filter | Find | ✕ Cancel

FIG. 10

| Routine protocols | My protocols | Protocol Designer | Reagent catalogs | Spectra | Tree |
|---|---|---|---|---|---|

Control panel

Add to inventory/edit  Get updates  ◇ No instrument yet  See: ☐ Mine  ☐ My Lab  ☑ Generic  Showing: 1 of 10

| Antibody/secondary | Avidin/streptavidin | Other fluorescent probes | | | | |
|---|---|---|---|---|---|---|
| Review | Private | Antigen molecule | Antibody reactivity | Antibody clone | Conjugate (color or hapten) | Antigen source species | Producer |
| | ☐ | CD2 | CD2 (RM2-5) | RM2-5 | PE | Mouse | BD Pharmingen |

FIG. 12

| Antibody/secondary | Avidin/streptavidin | Other fluorescent probes | | | | | |
|---|---|---|---|---|---|---|---|
| Review | Private | Antigen molecule | Antibody reactivity | Antibody clone | Conjugate (color or hapten) | Antigen source species | Producer |
| | ☐ | CCR6 | CCR6 (140706) | 140706 | Alexa Fluor 647 | Mouse | BD Pharmingen |
| | ☐ | CD 3 Molecula... | CD 3 Molecular Complex.. | 17A2 | PerCP-Cy5.5 | Mouse | BD Pharmingen |
| | ☒ | CD1d | CD1d (1B1) | 1B1 | Biotin | Mouse | BD Pharmingen |
| | ☒ | CD1d | CD1d (1B1) | 1B1 | Fluorescein (FITC) | Mouse | BD Pharmingen |
| | ☐ | CD1d | CD1d (1B1) | 1B1 | PE | Mouse | BD Pharmingen |
| | ☐ | CD2 | CD2 (RM2-5) | RM2-5 | PE | Mouse | BD Pharmingen |

Add to inventory/edit | Get updates | No instrument yet | See: ☒ Mine ☒ My Lab ☒ Generic | Showing: 6 of 19

FIG. 13

| | | | Add to inventory/edit | ⟳ Get updates | ◇ No instrument yet | See: ☑ Mine | ☑ My Lab | □ Generic | Showing: 5 of 19 |

| Antibody/secondary|Avidin/streptavidin|Other fluorescent probes |

| Review | Private | Antigen A Z* molecule | Antibody reactivity | Antibody clone | A Z* Conjugate (color or hapten) | Antigen source species | Producer |
|---|---|---|---|---|---|---|---|
| | □ | CCR6 | CCR6 (140706) | 140706 | Alexa Fluor 647 | Mouse | BD Pharmingen |
| | □ | CD 3 Molecula... | CD 3 Molecular Complex... | 17A2 | PerCP-Cy5.5 | Mouse | BD Pharmingen |
| | ☑ | CD1d | CD1d (1B1) | 1B1 | Biotin | Mouse | BD Pharmingen |
| | ☑ | CD1d | CD1d (1B1) | 1B1 | Fluorescein (FITC) | Mouse | BD Pharmingen |
| | □ | CD1d | CD1d (1B1) | 1B1 | PE | Mouse | BD Pharmingen |

FIG. 14

| Review | Private | Antigen molecule | Antibody reactivity | Antibody clone | Conjugate (color or hapten) | Antigen source species | Producer |
|---|---|---|---|---|---|---|---|
| | ☑ | CD1d | CD1d (1B1) | 1B1 | Biotin | Mouse | BD Pharmingen |
| | ☑ | CD1d | CD1d (1B1) | 1B1 | Fluorescein (FITC) | Mouse | BD Pharmingen |

Add to inventory/edit | Get updates | No instrument yet  See: ☑ Mine ☑ My Lab ☐ Generic  Showing: 2 of 19

Antibody/secondary | Avidin/steptavidin | Other fluorescent probes

FIG. 15

| Review | Private | A₂* Antigen molecule | Antibody reactivity | Antibody clone | A₁ Conjugate Z* (color or hapten) | Antigen source species | Producer |
|---|---|---|---|---|---|---|---|
| | ☐ | CCR6 | CCR6 (140706) | 140706 | Alexa Fluor 647 | Mouse | BD Pharmingen |
| | ☐ | CD 3 Molecula... | CD 3 Molecular Complex... | 17A2 | PerCP-Cy5.5 | Mouse | BD Pharmingen |
| | ☐ | CD1d | CD1d (1B1) | 1B1 | PE | Mouse | BD Pharmingen |

Add to inventory/edit | Get updates | No instrument yet   See: ☐ Mine ☒ My Lab ☐ Generic   Showing: 3 of 19

Antibody/secondary|Avidin/steptavidin|Other fluorescent probes

FIG. 16

| Review | Private | Antigen molecule | Antibody reactivity | Antibody clone | Conjugate (color or hapten) | Antigen source species | Producer |
|---|---|---|---|---|---|---|---|
| | ☐ | CD2 | CD2 (RM2-5) | RM2-5 | PE | Mouse | BD Pharmingen |

Antibody/secondary | Avidin/steptavidin | Other fluorescent probes

[Add to inventory/edit] [Get updates] / No instrument yet   See: ☐ Mine  ☐ My Lab  ☑ [Generic]   Showing: 1 of 19

FIG. 17

| Control panel | | Spectra | | Tree | | |
|---|---|---|---|---|---|---|
| Add to inventory/edit | Get updates | ⟋ No instrument yet | See: ☐ Mine | ☐ My Lab | ☐ Generic | Showing: 0 of 19 |

| Antibody/secondary | Avidin/steptavidin | Other fluorescent probes | | | | |
|---|---|---|---|---|---|---|
| Review | Private | A↓ Z↓ Antigen molecule | Antibody reactivity | Antibody clone | A↓ Z↓ Conjugate (color or hapten) | Antigen source species | Producer |

SYSTEM AND METHOD FOR SELECTING A MULTIPARAMETER REAGENT COMBINATION AND FOR AUTOMATED FLUORESCENCE COMPENSATION

CROSS-REFERENCE TO RELATED APPLICATIONS

This application claims the benefit of priority of U.S. Provisional Application No. 61/333,381, filed May 11, 2010, and U.S. Provisional Application No. 61/466,836, filed Mar. 23, 2011, each of which is a continuation-in-part of U.S. application Ser. No. 12/467,662, filed May 18, 2009, which claims priority to U.S. Provisional Patent Application Ser. No. 61/053,974, filed May 16, 2008. Each of these applications is incorporated by reference herein in its entirety.

STATEMENT OF GOVERNMENT FUNDING

This invention was made with government support under contract A1077395 awarded by the National Institute of Health. The Government has certain rights in this invention.

FIELD OF THE INVENTION

The invention relates generally to flow cytometry; automated fluorescence compensation, and reagent optimization.

BACKGROUND OF THE INVENTION

Flow cytometry relies on the measurement of signals from a combination of fluorescent molecules, or fluorescence-labeled reagents, to indicate the presence or amount of a single species of target molecule in a sample preparation. The fluorescence spectra of these fluorescent molecules or reagents frequently overlap and, as a result, it is necessary to apply computational methods to resolve the amount of fluorescence detected for each component of the reaction mixture. The most common protocols use a series of "single-stain" samples that individually provide independent measures of the fluorescence emitted by each of the fluorescent molecules, and a "matched series" of measurements for (putatively) non-fluorescent objects either present in the "single-chain" sample or independently obtained as non-stained objects. The slopes of the lines connecting the median (or mean) fluorescence values for the negative and positive measurement groups measured independently for each fluorescence is then used to estimate the amounts of overlap fluorescence that must be subtracted from a value observed when all of the fluorescent reagents are used together.

Fluorescence

Fluorescence is a cyclical process where a luminescence is generated by certain molecules in which the molecular absorption of a photon triggers the emission of another photon with a longer wavelength.

In the fluorescence process, certain molecules are capable of being excited, via absorption of light energy, to a higher energy state, also called an excited state. The energy of this short-lived excited state decays (or decreases) resulting in the emission of light energy. The emission of light via this process is to "fluoresce."

A fluorophore is a molecule that is capable of fluorescing. In its ground state, the fluorophore molecule is in a relatively low-energy, stable configuration, and it does not fluoresce. When light from an external source hits a fluorophore molecule, the molecule can absorb the light energy. If the energy absorbed is sufficient, the molecule reaches an excited state (high energy); this process is known as excitation. There are multiple excited states or energy levels that the fluorophore can attain, depending on the wavelength and energy of the external light source. Since the fluorophore is unstable at high-energy configurations, it eventually adopts the lowest-energy excited state, which is semi-stable. The excited lifetime (the length of time that the fluorophore is an excited state) is very short; the fluorophore rearranges from the semi-stable excited state back to the ground state, and part of the excess energy may be released and emitted as light. The emitted light is of lower energy, and of longer wavelength, than the absorbed light, thus the color of the light that is emitted is different from the color of the light that has been absorbed. De-excitation returns the fluorophore to its ground state. The fluorophore can absorb light energy again and go through the excited state to ground state process repeatedly.

Fluorescence Spectra

A fluorescent dye absorbs light over a range of wavelengths and every dye has a characteristic excitation range. This range of excitation wavelengths is referred to as the fluorescence excitation spectrum and reflects the range of possible excited states that the dye can achieve. Certain wavelengths within this range are more effective for excitation than other wavelengths. A fluorophore is excited most efficiently by light of a particular wavelength. This wavelength is the excitation maximum for the fluorophore. Less efficient excitation can occur at wavelengths near the excitation maximum; however, the intensity of the emitted fluorescence is reduced. Although illumination at the excitation maximum of the fluorophore produces the greatest fluorescence output, illumination at lower or higher wavelengths affects only the intensity of the emitted light; the range and overall shape of the emission profile are unchanged.

Fluorophore molecules, when excited, emit over a range of wavelengths. This range of wavelengths is referred to as the fluorescence emission spectrum. There is a spectrum of energy changes associated with these emission events. A molecule may emit at a different wavelength with each excitation event because of changes that can occur during the excited lifetime, but each emission will be within the fluorescence emission spectrum. Although the fluorophore molecules all emit the same intensity of light, the wavelengths, and therefore the colors of the emitted light, are not homogeneous. The emission maximum is the wavelength where the population of molecules fluoresces most intensely. The excited fluorophore also can emit light at wavelengths near the emission maximum. However, this light will be less intense.

The emission maximum for a given fluorophore is always at a longer wavelength (lower energy) than the excitation maximum. This difference between the excitation and emission maxima is called the Stokes shift. The magnitude of the Stokes shift is determined by the electronic structure of the fluorophore, and is characteristic of the fluorophore molecule. The Stokes shift is due to the fact that some of the energy of the excited fluorophore is lost through molecular vibrations that occur during the brief lifetime of the molecule's excited state. This energy is dissipated as heat to surrounding solvent molecules as they collide with the excited fluorophore.

Filters and Light Sources

Fluorescence requires a source of excitation energy. There are many light source options for fluorescence. Selecting the appropriate light source, and filters for both excitation and emission, can increase the sensitivity of signal detection.

Several types of light sources are used to excite fluorescent dyes. The most common sources used are broadband sources, such as, for example, mercury-arc and tungsten-halogen lamps. These lamps produce white light that has peaks of varying intensity across the spectrum. When using broadband white light sources it is necessary to filter the desired wavelengths needed for excitation; this is most often done using optical filters. Optical filters selectively allow light of certain wavelengths to pass while blocking out undesirable wavelengths. A bandpass excitation filter transmits a narrow range of wavelengths and may be used for selective excitation.

Laser excitation sources provide wavelength peaks that are well-defined, selective, and of high intensity allowing more selective illumination of the sample. The best performance is achieved when the dye's peak excitation wavelength is close to the wavelength of the laser. Several lasers commonly used include, for example, the compact violet 405 nm laser, 488 nm blue-green argon-ion laser, 543 nm helium-neon green laser, and 633 nm helium-neon red laser. Mixed-gas lasers such as, for example, the krypton-argon laser, can output multiple laser lines which may require optical filters to achieve selective excitation. High-output light-emitting diodes (LEDs) provide selective wavelengths, low cost and energy consumption, and long lifetime. Single-color LEDs are ideal for low-cost instrumentation where they can be combined with simple long pass filters that block the LED excitation and allows the transmission of the dye signal. However, the range of wavelengths emitted from each LED is still relatively broad and also may require the use of a filter to narrow the bandwidth.

Filters are important for selecting excitation wavelengths and for isolating the fluorescence emission emanating from the dye of interest. Stray light arising from sources other than the emitting fluorophores (for example, from the excitation source) interferes with the detection of the fluorescence emission. Stray light therefore must be contained to ensure only the fluorescence of the sample registers with the instrument's light-sensitive detectors. When a single dye is used, a long pass emission filter which selectively blocks out the excitation light to reduce background noise may be used to maximize the signal collected. If multiple dyes are used in the sample, a band pass emission filter can be used to isolate the emission from each dye.

Flow Cytometry

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus.

Flow cytometry utilizes a beam of light (usually laser light) of a single wavelength that is directed onto a hydro-dynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analyzing fluctuations in brightness at each detector (usually one for each fluorescent emission peak) it then is possible to derive various types of information about the physical and chemical structure of each individual particle. FSC correlates with the cell volume and SSC depends on the inner complexity of the particle (i.e. shape of the nucleus, the amount and type of cytoplasmic granules or the membrane roughness).

Flow Cytometers

Flow cytometers are able to provide real-time analysis of several thousand particles every second and can separate and isolate particles having specified properties actively. Single-cell suspensions first must be prepared to analyze solid tissues.

A flow cytometer has five main components: 1) a flow cell where a liquid stream (sheath fluid) carries and aligns the cells so that they pass single file through the light beam for sensing; 2) a light source, such as lamps (mercury, xenon); high power water-cooled lasers (argon, krypton, dye laser); low power air-cooled lasers (argon (488 nm), red-HeNe (633 nm), green-HeNe, HeCd (UV)); or diode lasers (blue, green, red, violet); 3) a detector and Analogue to Digital Conversion (ADC) system for generating FSC and SSC as well as fluorescence signals; 4) an amplification system (linear or logarithmic); and 5) a computer for analysis of the signals.

Early flow cytometers were generally experimental devices, but recent technological advances have created a considerable market for the instrumentation, the reagents used, such as, for example, fluorescently-labeled antibodies, and analysis software. Modern instruments usually have multiple lasers and fluorescence detectors; up to 4 lasers and 18 fluorescence detectors within a single instrument are available. Increasing the number of lasers and detectors allows for multiple antibody labeling, and can identify a target population by its phenotype. Certain instruments can take digital images of individual cells more precisely, allowing for the analysis of fluorescent signal location within or on the surface of cells.

The use of fluorescent molecules, such as fluorophore-labeled antibodies, in flow cytometry is a common way to study cellular characteristics. Within these types of experiments, a labeled antibody is added to the cell sample. The antibody then binds to a specific molecule on the cell surface or inside the cell. Finally, when the laser light of the appropriate wavelength strikes the fluorophore, a fluorescent signal is emitted and detected by the flow cytometer.

The data generated by flow cytometers can be plotted in a single dimension, to produce a histogram, or in two dimensional dot plots or even in three dimensions. The regions on these plots can be separated sequentially, based on fluorescence intensity, by creating a series of subset extractions (referred to as "gates"). Specific gating protocols exist for diagnostic and clinical purposes especially in relation to hematology. The plots often are made on logarithmic scales. Signals at the detectors have to be compensated electronically as well as computationally due to emission spectra overlap of different fluorophores. Data accumulated using the flow cytometer may be exported to be re-analyzed elsewhere, freeing up the instrument for other researchers to use.

Fluorescence Activated Cell Sorting (FACS)

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest. The term "FACS" is not a generic term for flow cytometry, although many immunologists inappropriately use the term FACS for all types of sorting and non-sorting applications.

Utilizing FACS, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Before the stream breaks into droplets the flow passes through a fluorescence measuring station where the fluorescent character of interest of each cell is measured. An electrical charging ring or plane is placed just at the point where the stream breaks into droplets. A charge is placed on the ring based on the prior light scatter and fluorescence intensity measurements, and the opposite charge is trapped on the droplet as it breaks from the stream. The charged droplets then fall through an electrostatic deflection system that diverts droplets into containers based upon their charge. In some systems the charge is applied directly to the stream while a nearby plane or ring is held at ground potential and the droplet breaking off retains charge of the same sign as the stream. The stream then is returned to neutral after the droplet breaks off.

Fluorescence Detection

For proper data interpretation, the fluorescent light recorded from one fluorescent source must be distinguished from that recorded from other fluorescent sources. For that reason, the ideal fluorophore has a fluorescence emission profile of a very intense, narrow peak that is well separated from all other emission peaks. Typical organic dyes and fluorescent proteins, however, have broad emission peaks that may overlap, (i.e., emit some light in the same wavelength range). This spectral overlap may compromise data and analysis.

Multiple Fluorescent Signals

Background fluorescence, which may originate from endogenous sample constituents (autofluorescence) or from unbound or nonspecifically bound reagents, may compromise fluorescence detection severely. Briefly, excitation (EX) in overlapping absorption bands A1 and A2 produces two fluorescent species with spectra E1 and E2. The detection of autofluorescence (i.e., the A2-E2 spectra) can be minimized either by selecting filters that reduce the transmission of E2 relative to E1 or by selecting reagents that absorb and emit at longer wavelengths. Although narrowing the fluorescence detection bandwidth increases the resolution of E1 and E2, it also compromises the overall fluorescence intensity detected. Signal distortion caused by autofluorescence of cells, tissues and biological fluids is minimized most readily by using reagents that can be excited at >500 nm. At longer wavelengths, light scattering by dense media such as tissues is much reduced, resulting in greater penetration of the excitation light. The use of optical filters isolate quantitative emission signals S1 and S2.

Multicolor labeling incorporates the use of two or more probes to monitor simultaneously different biochemical functions. This technique has major applications in flow cytometry, DNA sequencing, fluorescence in situ hybridization (FISH) and fluorescence microscopy. Signal isolation and data analysis are facilitated by maximizing the spectral separation of the multiple emissions (E1 and E2). Consequently, fluorophores with narrow spectral bandwidths, such as, for example, Alexa Fluor dyes and BODIPY dyes (Molecular Probes, Eugene, Oreg.), are useful in multicolor applications. An ideal combination of dyes for multicolor labeling would exhibit strong absorption at a coincident excitation wavelength and well-separated emission spectra. Unfortunately, it is not simple to find single dyes with the requisite combination of a large extinction coefficient for absorption (meaning a parameter defining how strongly a substance absorbs light at a given wavelength, expressed per mass unit or per molar concentration) and a large Stokes shift (meaning the difference (in wavelength or frequency units) between positions of the band maxima of the absorption and emission spectra of the same electronic transition, see infra).

Signal Amplification

Fluorescence signals may be amplified by increasing the number of fluorophores available for detection. However, simply increasing the probe concentration can be counterproductive and often produces marked changes in the probe's chemical and optical characteristics. The effective intracellular concentration of probes loaded by bulk permeabilization methods usually is much higher (>10-fold) than the extracellular incubation concentration. Additionally, the increased labeling of proteins or membranes ultimately leads to precipitation of the protein or gross changes in membrane permeability. Antibodies labeled with more than four to six fluorophores per protein may exhibit reduced specificity and reduced binding affinity. At high degrees of substitution, the extra fluorescence obtained per added fluorophore typically decreases due to self-quenching.

Compensation

Compensation is the mathematical process for correcting multiparameter flow cytometric data for spectral overlap. This overlap ("spillover") results from the use of fluorescent dyes that are measurable in more than one detector; this spillover is correlated by a constant ("spillover coefficient"). The process of compensation is a simple application of linear algebra to correct for spillovers of all dyes into all detectors, such that on output, the data are effectively normalized so that each parameter contains information from a single dye.

Generally, the ability to process data is most effective when the visualization of data is presented without unnecessary correlations (i.e., when displaying graphs of one or two parameters there is no contribution of other (perhaps undisplayed) parameters to the distributions being shown). This becomes more problematic upon inclusion of two or more interacting parameters; the presence of multiple fluorescent signals must be accommodated within any fluorescence detection system for accurate quantification and analysis. Fluorescence is recorded using an emission filter chosen to collect the maximum amount of light coming from the fluorophore of interest and to exclude as much light as possible from other nearby fluorophores or fluorescent sources. While an emission filter efficiently captures the emission peak of the target fluorophore, it also may collect the light from one or more additional fluorophores due to spectral overlap in the emission profiles. Such data needs to compensated, i.e., a percentage of fluorescence is subtracted from one channel measuring a fluorophore and from a second channel measuring the fluorescence of the second (or multiple) fluorophore, such that the contribution of the incidental fluorescence is removed. Proper or correct compensation is achieved when the compensated data in each detector have no bias in the fluorescence distribution that is related to the intensity measured in any other detector.

Depending upon the instrument and software used, compensation may be set either in the instrument hardware before the sample is run or within the software after data collection. Every fluorophore combination that shows spectral overlap must be compensated.

Multicolor flow cytometry yields measurements of fluorescence from individual cells; however, biologists generally are interested in the amount of reagent bound to each individual cell. The process of transforming multicolor fluorescence measurements to yield estimates of the amounts of different dyes present is referred to as "fluorescence compensation"; To determine the amount of compensation required to correct the fluorescence data, single-color samples (either aliquots of the cell sample stained with each fluorophore separately or microspheres that capture an individual reagent) are utilized and analyzed in parallel with the experimental samples stained with multiple fluorophores.

Fluorescence Compensation

Although previous studies have attempted to measure two different dyes excited by the same laser but emitting at different wavelengths, it became apparent in such studies that each dye contributed some signal on each detector. It generally is believed that this was not a result of inadequacies in optical filters, but a fundamental limitation in the chemical physics of the dyes leading to emission of some light over a range of wavelengths broader than the peak emission zone. Although a FACS detector (channel) is intended to detect the light emitted by a given dye on a single cell, it also will detect light emitted by any other dye that is associated with the cell, excited by the same laser, and capable of emitting light at wavelengths that pass through the optical bandpass filter for the channel. The dyes, lasers and optical filters are chosen so that each detector is optimally sensitive to one dye, but, generally, each dye also will produce some signal on one or more other detectors. Therefore, to obtain an accurate estimate of the signal due to the dye of interest on a particular detector, it is necessary to evaluate the signal contributed by spectral overlap of other dyes and subtract that from the initial signal recorded by the detector.

Subsequently, studies focused on the constant ratio produced by the amount of signal produced by one dye on a detector intended for another dye, with the signal of the first dye on its own detector. This allowed for "compensated" outputs to be determined where the spectral overlap was adjusted; however these compensated outputs were proportional only to the amount of the dye of interest.

Two basic methods have been used to accomplish spectral overlap correction: analog compensation and computed compensation. Analog circuitry in the cytometer itself initially was used since fluorescence compensated data was needed for cell sorting with multiple dyes and the compensated data could be displayed to monitor data collection. However, if compensation settings were incorrect during the run, they could not be revised. Computed compensation starting with uncompensated measurements could be carried out after the fact and, if necessary, revised, but its use on cytometers themselves initially was limited by the available computing power.

Analog and computed compensation rely on the measurement of compensation control samples in order to specify the spectral overlap correction factors for each dye on each detector. The control samples consist of cells or particles stained separately with each of the dyes used in the experiment. A completely unstained sample also is useful usually. Analysis of data from these control samples yields spectral overlap factors between each dye and each detector, and the whole set of overlaps can be expressed as a spectral overlap matrix. Mathematically, fluorescence compensation is carried out by multiplying a vector consisting of the detector/color measurements for a particular cell by the inverse of the spectral overlap matrix (the "compensation matrix") to obtain the calculated amount of each dye on that cell as a new vector.

The number of spectral overlaps to be evaluated and corrected increases rapidly with increasing numbers of dyes and detectors. For example, for N dyes on N detectors, there are $N^2$ possible signal contributions, N of which represent each dye on its intended detector, and the other $N^2-N$ represent spectral overlaps. While two dyes give only two overlaps, ten dyes have 90 possible overlaps. Many of the overlaps are very small and can be ignored, but the number of relevant overlaps quickly goes beyond anything reasonable to set by hand, leading to a demand for computerized assistance in carrying out fluorescence compensation.

Compensation Errors

Correct compensation for more than two colors almost never can be achieved using the standard interface of adjusting compensation coefficients (rather than spillover coefficients), because of the interdependence of these values. Studies have reported that even properly compensated data may appear to be undercompensated. There are at least two distinct types of errors that contribute to imprecise compensation: errors arising from (1) photon-counting statistics, and (2) measurement errors. These are distinct in that the former are nonlinear, while the latter are linear. It generally is believed that it is not possible to properly set compensation by visual methods (i.e., relying on dot plots or histograms); nor is it possible to accurately analyze data using quadrant gates or control samples based on isotype controls in all channels. Importantly, this holds true irrespective of the use of newer digital electronics that obviate the use of log amplifiers (a significant source of measurement error).

A fundamental measurement error that never can be overcome is one arising from counting statistics. For most cytometry applications, the number of photoelectrons in the photomultiplier tube (PMT) detector is typically in the range of 1 to about $10^5$, depending on the signal intensity. For example, autofluorescence in the fluorescein or phycoerythrin detectors (for lymphocytes) is typically below 10 photoelectrons. The error in this measurement must be at least as great as the counting error, which is the square-root of the count (i.e., $10 \pm 3.2$ ($\pm 32\%$)). Even at $10^4$ photoelectrons, which puts the signal into the third decade of fluorescence, the counting error is $\pm 1\%$. These measurement errors contribute to the spread in compensated parameters.

Studies have reported that decreasing the number of photons (or photoelectrons at the first PMT dynode) has several effects on compensation. It has been reported that (1) reducing spillover decreases the "error" in the compensated distribution concomitantly; (2) as the number of photons available to the primary detector decreases, the error in the distribution increases concomitantly; (3) the spread downward occurs at a much lower intensity than the spread upwards (as is the case for proportionate errors); and (4) the spread upward occurs at a relative log-log slope of 1:2 because the photon-counting error is proportional to the square root of the measurement intensity (i.e., nonlinear). Thus, this visualization artifact cannot be corrected by overcompensating the data, because compensation is a linear process.

Compensation Error Correction

It generally is believed that no electronics can overcome the fundamental counting error inherent in measuring signal levels. This nonlinear error contribution in the data always will be present and lead to the spread of compensated data.

The degree to which the errors are apparent depends principally on two factors: the degree of spillover, and the brightness of the signal. Minimizing these errors can be accomplished by using fluorescent dyes that are as bright as possible, with as little spectral overlap as possible. Likewise, optimizing light collection will improve signal detection. If postacquistion compensation is necessary, then storing the data in as many channels as possible also may minimize error. However, the spreading of compensated data may continue to impact significantly the analysis and interpretation of data. For example, where this error is present, the use of linear "quadrant gates", or any gate based on a completely unstained sample, would lead to erroneous results, since at higher intensities, the autofluorescence distribution will spread up into the "positive" gate. It generally is believed that the best control is to stain cells with all reagents except for the one of interest in order to determine the exact range of the negative population. This type of control may be termed "fluorescence minus one" (FMO). A nonlinear gate can be drawn based on an FMO control, and applied to the fully stained sample to determine which events are positive.

Some flow cytometry data analysis packages have offered software-assisted compensation based on positive-negative differences. The typical procedure has been for the user to apply gates to data on single stained control samples and to select cell populations that are positive and negative for each single dye to be used in multi-color staining. The software then computes the median (or mean) fluorescence for each population. The differences between the corresponding positive-negative population pairs in each data dimension are used to evaluate the elements of the spectral overlap matrix, and the compensation then can be applied to any cell sample stained with the appropriate dyes.

Some commercial software (such as, for example, FlowJo (Treestar, Inc., Ashland, Oreg.)) requires user interaction to analyze the compensation control samples and to identify appropriate gated populations but proceeds automatically from there. Other software (such as Diva (BD Biosciences)) includes partial automation of the positive-negative population difference method for evaluating the spectral overlap matrix in which a positive peak is found automatically and gated in a 1-dimensional fluorescence histogram of each compensation control sample after user-specified light scatter gating.

There are several problems with existing methodology for estimating fluorescence compensation. For example, existing methods rely only upon gated population means or medians to estimate the matrix coefficients. Further, most existing methods rely on subjective gating to exclude inappropriate events and to specify appropriate populations for evaluation of compensation coefficients. Additionally, existing methods of estimating coefficients rely on subjective human evaluation for validation of the quality of the resulting measurements, and fail to provide errors of estimates for the coefficients.

The described invention, which avoids many of the pitfalls of the current methods of determining fluorescence spectra overlap, provides a model-based approach to compensation that addresses these problems, uses compensation computation to define cocktails to minimize the effect of compensation, and uses criteria of availability to provide a rank-ordered list of reagent combinations. It provides a fully automatic method for computing slopes based on the use of all measurements taken for the sample; it does not rely on gating or other methods to distinguish signals from fluorescent versus non-fluorescent objects. Instead, the described invention utilizes all of the measurements to compute the required slopes. Further, while current methods do not enable computation of the accuracy of resultant slopes, the described invention automatically provides quality metrics that report whether the slopes computed for any of the fluorescence spectra are accurate enough to be useful over the necessary dynamic range. Additionally, while current methods do not readily provide a way to compute fluorescence overlap corrections for measurements in which full fluorescence spectra are taken for each item (as opposed to a limited series of measurements of "peak channel" fluorescence), the described invention is fully applicable with full fluorescence spectra measurements. Furthermore, the described invention provides a method for determining the absolute detector sensitivity in terms of number of photons. This allows for an upper bound on the quality of signal that can be obtained.

The described invention also provides personalizable, customizable and automatable methods to replace the arduous and sometime intractable methods used currently in flow cytometry and other multiparameter assays. These assays, which reveal markers (target molecules) co-expressed in or on cells or particles of interest, are widely used in research and medicine to discriminate the various types of cells present in blood and other organs. However, they have yet to achieve their full potential, largely because the complex knowledge and functions skills needed to perform the assays effectively restricts their current use to large medical centers and research institutions and deters development of new assays that could provide even greater benefit.

To overcome these restrictions, the invention substitutes knowledge-based and knowledgeable computer technology that simplifies the application and extension of flow cytometry and other fluorescence-based assays and hence makes these assays more accessible to the laboratories whose personnel are only modestly skilled in developing and applying them. Thus, the invention provides a series of interconnected software utilities that facilitate the various assay steps as they are performed. These range from early stage utilities that provide help with protocol design tasks such as the acquisition, selection and optimization of reagent combinations (stain sets) to late stage utilities that enable transfer of the protocol information needed during data collection to annotate data and apply automated fluorescence compensation to initiate data analysis.

The invention provides extensive help for protocol design. Using built in, supplied or extracted knowledge about marker expression, reagent specificity, fluorescence spectra and compensation, instrument detection capabilities and other factors, the invention can list all possible reagent combinations (stain sets) constructible from available reagents. Furthermore, it can rank the stain sets according to predicted optimal efficiency for detecting individual markers or cell types (for example, by evaluating likely interference due to fluorescence overlap among reagents detecting markers on the same target cell). In essence, the invention allows users to indicate the markers (e.g., cell surface determinants) that they want the stain set to detect and to specify expected levels of marker expression on cells that will be stained. It then returns the possible reagent combinations that could accomplish this task and indicates which stains sets are likely to be most efficient for this purpose.

To further release users from difficult and tedious tasks, the invention allows users to point-and-click or drag-and-drop to select and re-use reagents, subjects, samples, keywords and other assay items. In this way, it provides users with the tools to create and print full, executable assay protocols and to store these in machine readable format. To further facilitate selections, the invention displays reagents and other assay items in unique, highly flexible and personalizable tree-table formats that efficiently communicate necessary knowledge. In addition, the invention helps users to transfer protocol information to data collection instruments and to add the information to data files and enables archiving and long-term maintenance of well-annotated archived data. To help users manage local reagent supplies and select and purchase additional reagents, the invention provides an automated "personal reagent shopper" that can maintain and search catalogs of commercial reagents to locate and import reagents that are compatible with detection instrument capabilities and with reagents that have already been selected into the stain set. In addition, to help users avoid costly but common omissions of key assay controls, the invention automates the specification and inclusion of control samples necessary for fluorescence compensation computations and for analysis of data from samples that show minimal staining with key reagents on key subsets.

Thus, with these and other automated capabilities described herein, the invention provides for performance of high quality multiparameter flow cytometry and other fluorescence-based assays that currently only are accessible to practitioners who acquire the knowledge necessary to master the intricacies of the technology and acquire the knowledge to perform these assays well. Since such assays are becoming increasingly more important in medical practice, and since they are crucial to the development of cancer therapies, stem cell transplantation methods and modern approaches to the treatment of infectious diseases, the invention has a strong practical significance that couples well with and in addition to opening key methods for using computer technology to the advances it brings to the ways computer technology can used to break down barriers to optimal use of powerful biomedical instrumentation.

SUMMARY

According to one aspect, the described invention provides a computing device comprising: a processor; a storage medium for tangibly storing thereon program logic for execution by the processor, the program logic comprising: (a) logic executed by the processor for displaying a protocol summary page enabling a user to enter descriptive information about an experiment; (b) logic executed by the process for displaying a subject and sample page enabling the user to enter subject names, sample names, and keyword values; (c) logic executed by the processor for displaying a stain set entry page enabling the user to: (i) select a data collection instrument whose pre-entered capabilities define limits of reagents that can be included in stain sets in the experiment; (ii) enter markers to be detected by the stain set; and (iii) select reagents to be included in the stain set; (iv) enter expected properties for the stain set targets; (d) logic executed by the processor for computing and ranking of possible stain sets; (e) logic executed by the processor for displaying a list of feasible stain sets ranked according to how well each stain set is likely to discriminate cells or particles with an expression level property indicated by the user; (f) logic executed by the processor for inspecting remaining combinations and for developing a set of controls based on a need for single stain fluorescence compensation samples for dyes used in the experiment and based on the need for fluorescence minus one (FMO) controls for sample/stain set combinations; and (g) logic executed by the processor for printing, recording, or exporting machine-readable protocol output files for storage and passage to data collection instruments.

According to one embodiment, the logic for displaying a stain set entry page enabling the user to enter markers to be detected by the stain set further comprises enabling the user to select a marker by name from a first level of a tree. According to another embodiment, the logic for displaying a stain set entry page enabling the user to enter markers to be detected by the stain set further comprises enabling the user to select an antibody or other marker detector from a second level of the tree. According to another embodiment, the logic for displaying a stain set entry page enabling the user to enter markers to be detected by the stain set further comprises enabling the user to select a dye conjugate for a marker detector or an unconjugated detector from a third level of the tree. According to another embodiment, the logic for displaying a stain set entry page enabling the user to enter markers to be detected by the stain set further comprises enabling the user to select a specific lot of a conjugated or unconjugated detector from a fourth level of the tree. According to another embodiment, the computing device further comprises determining the stain set. According to another embodiment, the determining of the stain set further comprises determining sensitivity to staining conditions that influence dyes. According to another embodiment, the computing device further comprises logic executed by the processor for ranking a stain set list and displaying the stain set list in a table in which each row shows the stain set rank, a score assigned to the stain set, and the reagents contained in the stain set. According to another embodiment, the computing device further comprises logic executed by the processor for displaying a page on which the stain set the user has chosen or constructed and the samples to be stained with the stain sets are combined such that each sample is stained with each stain set. According to another embodiment, the computing device further comprises logic executed by the processor for displaying a stain set-sample combination and a control sample list in a plate-rack layout that provides a plan for executing the experiment. According to another embodiment, the computing device further comprises logic executed by the processor for permanently recording the stain set that is constructed and for enabling recall of previous stain sets. According to another embodiment, the computing device further comprises logic executed by the processor for enabling copying and editing of the recalled stain sets for editing and reuse in subsequent experiments. According to another embodiment, the computing device further comprises logic executed by the processor for automatically testing recalled stain sets for compatibility with current samples and instrumentation. According to another embodiment, the computing device further comprises logic executed by the processor for automatically implementing re-optimization of a stain set composition to accord with current conditions.

According to another aspect, the described invention provides a computer-readable storage medium tangibly storing thereon computer program instructions capable of being executed by a computer processor of a computing device, the computer program instructions defining the steps of: (a) specifying a plurality of markers to be detected by a plurality of reagents; (b) specifying at least one expected level of expression of one or more markers in a plurality of markers expected to be detected on or in each of a plurality of cells; (c) generating a plurality of reagent combinations comprising a plurality of reagents to detect the plurality of markers of step (a), wherein the reagent combinations are ranked according to at least one user-defined or system-defined criterion; and (d) providing a rank-ordered list of combinations.

According to another aspect, the described invention provides a method for selecting an optimal multimarker reagent combination for the identification and quantification of at least one molecule in or on at least one cell with or without reference to at least one property of at least one instrument-measurable atom, molecule, and molecular complex associated with the reagent combination, the method comprising: (a) using a user interface device, specifying a plurality of markers to be detected by a plurality of reagents; (b) using a user interface device, specifying at least one level of expression of one or more marker in the plurality of markers expected to be detected on or in each of a plurality of cells; (c) using a computing device, generating a plurality of reagent combinations each comprising the plurality of reagents to detect the plurality of markers in (a), wherein the reagent combinations are ranked according to at least one user-defined or system-defined criterion; and (d) using a computing device, providing a rank-ordered list of the reagent combinations.

According to one embodiment of the method, at least one of steps (a), (b), (c), and (d) is performed using a computer. According to another embodiment, at least one of steps (a), (b), (c), and (d) is performed automatically. According to another embodiment, at least one molecule is an activation marker, an antigen, a cell surface marker, a chromophore, a differential label, a dye, or a stain. According to another embodiment, an expected level of expression of the at least one molecule on at least one cell type to be targeted by a stain set can be arbitrarily selected manually from a list of expression levels displayed by a computer. According to another embodiment, the instrument-measurable atom, molecule or molecular complex is an antigen, an activation marker, a cell surface marker, a chromophore, a differential label, a dye or a stain. According to another embodiment, step (a) further comprises the steps: (i) specifying, using a computer, a plurality of reagents that can detect or participate in the detection of one or more of the plurality of markers; (ii) specifying, using a computer, at least one fluorescent dye or other instrument-measurable atom or molecule associated with each reagent; (iii) specifying, using a computer, a plurality of measurement instruments and the properties or measurement capabilities of each measurement instrument. According to another embodiment, at least one of steps (i), (ii) and (iii) is performed by a computer. According to another embodiment, step (i) the user interactively enters or chooses at least one marker to be detected by at least one stain set by entering at least one desired marker name or selecting at least one marker from a selection widget available on each row of a table-like structure in a column that displays markers already selected by at least one other method. According to another embodiment, step (d) further comprises automatically estimating fluorescence compensation based on the fluorescence properties of the reagent combinations. According to another embodiment, specifying step (a) is based on information from a genomic screen. According to another embodiment, the at least one user-defined or system-defined criterion is at least one of spectral interactions, detectors on an instrument, illumination sources on an instrument, amount of reagent on-hand, known reactivities of reagents in each reagent combination, known cross-reactivities of reagents in each reagent combination, properties of each reagent in each reagent combination, known sensitivities of reagents in each combination to treatments employed during the staining process, known sensitivities of reagent targets to treatments employed during the staining process, known or presumed amounts of reagent targets on particular cells or particles on which reagent targets are expressed, known reagent availability, availability of data acquisition and analysis capabilities, species of target cells, and species of reagent source. According to another embodiment, step (d) further comprises the step of selecting an optimal reagent combination. According to another embodiment, the at least one property is fluorescence and fluorescence properties are selected from the group consisting of fluorochromes, lasers, filters, dye spectra, spectral overlap detection capabilities, and sensitivity of a fluorochrome to destruction by a treatment that occurs prior to, during, or after a given staining step. According to another embodiment, generating of the plurality of reagent combinations in step (c) further comprises the steps: (i) transmitting cell surface marker information based on a surface marker characteristic of at least one type of cell to a data repository; (ii) receiving reagent information from the data repository according to the transmitted cell surface marker information; and (iii) generating the plurality of reagent combinations according to the reagent information from the data repository. According to another embodiment, at least one of steps (i), (ii) and (iii) is performed by a computer. According to another embodiment, ranking step (d) is performed automatically according to a predetermined efficacy with regard to at least one type of cell. According to another embodiment, ranking step (d) is performed manually according to user generated preferences. According to another embodiment, the automatic ranking of the plurality of reagent combinations further comprises: (i) determining whether an amount of each of the plurality of ingredients required for each of the plurality of reagent combinations is sufficient or insufficient; (ii) excluding each of the plurality of reagent combinations for which the available quantity of any of the plurality of ingredients is insufficient; and (iii) ranking the plurality of reagent combinations that have not been excluded. According to another embodiment, the method is used for flow cytometry, and wherein the method further comprises identifying at least one type of cell by selecting at least one type of cell from the cells to react with at least one of the plurality of reagent combinations according to at least one surface marker characteristic of at least one type of cell.

According to another aspect, the described invention provides a method for generating multimarker experiment data for identification and quantification of at least one molecule in or on at least one cell with or without reference to at least one fluorescence property of at least one instrument-measurable atom, molecule, or molecular complex associated with a reagent combination, the method comprising steps: (a) using a computing device, generating a plurality of reagent combinations each comprising a plurality of reagents to detect a plurality of markers; (b) using a computing device, specifying at least one level of expression of one or more marker in a plurality of markers expected to be detected on or in each cell in the plurality of cells; and (c) using a computing device, generating a rank-ordered list of reagent combinations ranked according to at least one user-defined or system-defined criterion.

According to one embodiment of the method, at least one of steps (a), (b), and (c) is performed using a computer. According to another embodiment, at least one of steps (a), (b), and (c) is performed automatically. According to another embodiment, step (a) further comprises the steps: (i) specifying a plurality of reagents that can detect or participate in the detection of one or more of the plurality of markers; (ii) specifying at least one fluorescent dye or other instrument-measurable atom or molecule associated with each reagent; (iii) specifying plurality of measurement instruments and the properties or measurement capabilities of each measurement instrument. According to another embodiment, at least one of steps (i), (ii) and (iii) is performed by a computer. According to another embodiment, step (c) further comprises the step of selecting an optimal reagent combination. According to another embodiment, at least one user-defined or system-defined criterion is at least one of spectral interactions, detectors on an instrument, illumination sources on an instrument, amount of reagent on-hand, known reactivities of reagents in each reagent combination; known cross-reactivities of reagents in each reagent combination, properties of each reagent in each reagent combination, available analysis capabilities, and species of an instrument. According to another embodiment, the method further comprises generating an annotated experiment plan based on at least one type of cell and the optimal reagent combination, the method comprising at least one of steps by using the computer for text entry, (i) pointing-and-clicking or dragging-and-dropping subjects, samples, and keywords for the experiment; (ii) generating a ready-to-use pipetting plan based on the subjects, samples, and keywords; and (iii) printing the ready-to-use pipetting plan. According to another embodiment, at least one of steps (i), (ii) and (iii) are performed by a computer. According to another embodiment, the generated experiment plan of step (i) is transferred to an instrument where the experiment plan is displayed via software on the instrument, and wherein the generated experiment data and the generated experiment plan are automatically linked and/or stored in the same directory. According to another embodiment, the generated experiment plan is transferable to a DiVa data collection software on the instrument; According to another embodiment, the DiVa software displays sample names, keywords, reagent labels, and at least one fluorescent dye while the experiment data is being generated; wherein the DiVa software labels the generated experiment data; and wherein the generated experiment data is stored in data files. According to another embodiment, the data files are automatically transferable to a well-managed online archive; wherein the archive automatically catalogs the data files; and wherein the archive includes a server computer to allow a user to access the data files via a computer network. According to another embodiment, the method further comprises step: (i) generating analysis results based on the generated experiment data and the generated experiment plan, wherein the analysis results are stored in the same directory as the generated experiment data and the generated experiment plan. According to another embodiment, the method comprises steps: (i) generating at least one hyperlink to the data files on the archive to access the data files via a computer network; and (ii) storing at least one hyperlink on the computer, wherein at least one hyperlink is automatically linked to the generated experiment data and the generated experiment plan, and wherein at least one hyperlink is stored in the same directory as the analysis results. According to another embodiment, step (i) further comprises steps: (a) determining a dilution of the reagent combination; (b) calculating a volume of the reagent combination; (c) calculating a volume of a sample population of cells; and (d) determining a quantity of at least one fluorescent dye for use in creating a multimarker Hi-D stain set for flow cytometry or fluorescence microscopy. According to another embodiment, at least one of steps (i), (ii), and (iii) is performed by a computer. According to another embodiment, the computer allows a user to rapidly design or modify the multimarker experiment data. According to another embodiment, the multimarker experiment data includes a multimarker stain set that combines twelve or more reagents. According to another embodiment, ranking step (c) identifies at least one type of cell or to segregate at least one type of cell from the population of cells. According to another embodiment, ranking step (c) is performed manually according to user generated preferences. According to another embodiment, ranking step (c) is performed automatically according to a predetermined efficacy with regard to at least one type of cell. According to another embodiment, the method further comprises steps: (i) using a personal reagent shopper to search a data repository via a computer network to determine whether at least one ingredient for at least one of the reagent combinations are available from at least one supplier; and (ii) ordering a quantity of at least one ingredient from at least one supplier. According to another embodiment, a user can search the plurality of reagent combinations to find a particular reagent combination. According to another embodiment, step (c) the best dye combination provides for a minimal an amount of correction needed due to overlap of fluorescent dyes.

According to another aspect, the described invention provides a system to streamline the locating, ordering, and re-ordering of at least one reagent from at least one supplier for use in an experiment when an available amount on hand is insufficient for the experiment, the system comprising: (a) a computer connected to a data repository via a computer network; and (b) a personal reagent shopper usable by the computer to search the data repository for at least one reagent, wherein the personal reagent shopper orders a quantity of at least one reagent from at least one supplier when the available amount on hand is insufficient for the experiment.

According to one embodiment, (b) the personal reagent shopper orders a quantity of at least one reagent manually. According to another embodiment, (b) the personal reagent shopper orders a quantity of at least one reagent automatically. According to another embodiment, (b) the personal reagent shopper orders a second quantity of at least one reagent from a secondary supplier when an amount available from at least one supplier is insufficient for the experiment. According to another embodiment, the personal reagent shopper orders a quantity of at least one reagent manually. According to another embodiment, the personal reagent shopper orders a quantity of at least one reagent automatically.

According to another aspect, the described invention provides a method for determining the effective spectrum matrix used in a flow cytometer including a plurality of detectors, the method comprising steps: (a) measuring the autofluorescence of a set of unstained cells or reagent capture particles with each of the plurality of detectors of the flow cytometer, wherein autofluorescence data is obtained from each detector and stored in a data storage device; and wherein the mean and standard deviation of the autofluorescence data measured by each detector is determined using a computing device; (b) measuring the fluorescence of a set of cells or particle samples labeled singly with each fluorochrome of a plurality of fluorochromes, wherein each fluorochrome of the plurality of fluorochromes is assigned a primary detector of a flow cytometer, wherein fluorescence data is obtained from each assigned primary detector of each fluorochrome of the plurality of fluorochromes; and (c) analyzing the fluorescence data from each assigned primary detector of each fluorochrome of the plurality of fluorochromes of step (b), the analysis comprising: (i) excluding any measurement of fluorescence wherein the fluorescence is within 10% of the maximum observable signal on any detector of the flow cytometer; and (ii) excluding any measurement of fluorescence recorded on the primary detector for the fluorochrome where the fluorescence recorded is less than two standard deviations above the mean of the autofluorescence data of step (a), thereby determining the effective spectrum matrix used in flow cytometry for fluorescence compensation.

According to one embodiment, the method further comprises the steps: (d) analyzing the fluorescence data from each assigned primary detector of each fluorochrome of the plurality of fluorochromes of step (c), the analysis comprising steps: (i) assigning the background value for each assigned primary detector of each fluorochrome of the plurality of fluorochromes to a value of 0, wherein the standard deviation of each fluorescence measurement from each assigned primary detector of each fluorochrome is estimated as being proportional to the square root of the absolute signal level on the primary detector of the fluorochrome; (ii) using a robust fitting procedure to fit a line through the mean of the autofluorescence data of each detector, wherein errors are scaled using the estimates computed in step (i); (iii) estimating the background signal level by using the medians of the squared scaled errors of the brightest half of the fit data and the squared errors of the autofluorescence data around their mean; (iv) computing an improved estimate of the standard deviation of each event as the proportional to square root of the absolute signal level on the primary detector plus the estimated background; (v) computing the median squared scaled error of fit with a robust fitting procedure to fit a line wherein errors are scaled using each point; (vi) determining the photo electron sensitivity scaling using the median squared scaled error of fit of step (v), wherein all errors are rescaled so that the resulting errors are chi-squared distributed with one degree of freedom; and (vii) totaling the square scaled error from all detectors for each event, wherein outliers are excluded. According to another embodiment, the method further comprises the steps: (e) fitting a least squares line to the remaining data constrained to pass through the mean of the autofluorescence using the computed estimated standard deviations, wherein the slope of the line provides one coefficient in the effective spectrum matrix.

According to another aspect, the described invention provides a method for selecting an optimal multimarker reagent combination for the identification and quantification of at least one molecule in or on at least one cell with or without reference to at least one property of at least one instrument-measurable atom or molecule associated with the reagent combination, the method comprising: (a) using a user interface device, specifying a plurality of markers to be detected by a plurality of reagents; (b) using a user interface device, specifying at least one measurable instrument; (c) using a computing device, generating a plurality of reagent combinations each comprising at least one of the plurality of reagents to detect the plurality of markers in (a), wherein the reagent combinations are ranked according to at least one user-defined or system-defined criterion; and (d) using a computing device, providing a rank-ordered list of the reagent combinations.

According to one embodiment of the method, step (a) further comprises specifying at least one level of expression of one or more marker in the plurality of markers expected to be detected on or in each of a plurality of cells. According to another embodiment, step (c) the reagent combinations further comprise a list of available reagents and a list of needed reagents. According to another embodiment, step (c) further comprises comparing the list of needed reagents against at least one data repository of at least one supplier.

BRIEF DESCRIPTION OF THE DRAWINGS

FIG. 4 shows a screencap of the options available when right-clicking over a node of the navigation tree.

FIG. 5 shows a screencap of a window of the customizable search interface that facilitates population of the navigation tree, the creation of tabs, and searches.

FIG. 10 shows a screencap of a window of the user interface that includes check boxes, columns, and an operation button.

FIG. 12 shows a screencap of an embodiment of a window of a filter check box where all check boxes are checked.

FIG. 13 shows a screencap of an embodiment of a window of a filter check box where only "mine" and "my lab" check boxes are checked.

FIG. 14 shows a screencap of an embodiment of a window of a filter check box where only "mine" is checked.

FIG. 15 shows a screencap of an embodiment of a window of a filter check box where only "my lab" is checked.

FIG. 16 shows a screencap of an embodiment of a window of a filter check box where only "generic" is checked.

FIG. 17 shows a screencap of an embodiment of a window of a filter check box where nothing is checked.

DETAILED DESCRIPTION OF THE INVENTION

Glossary

Figure 1:
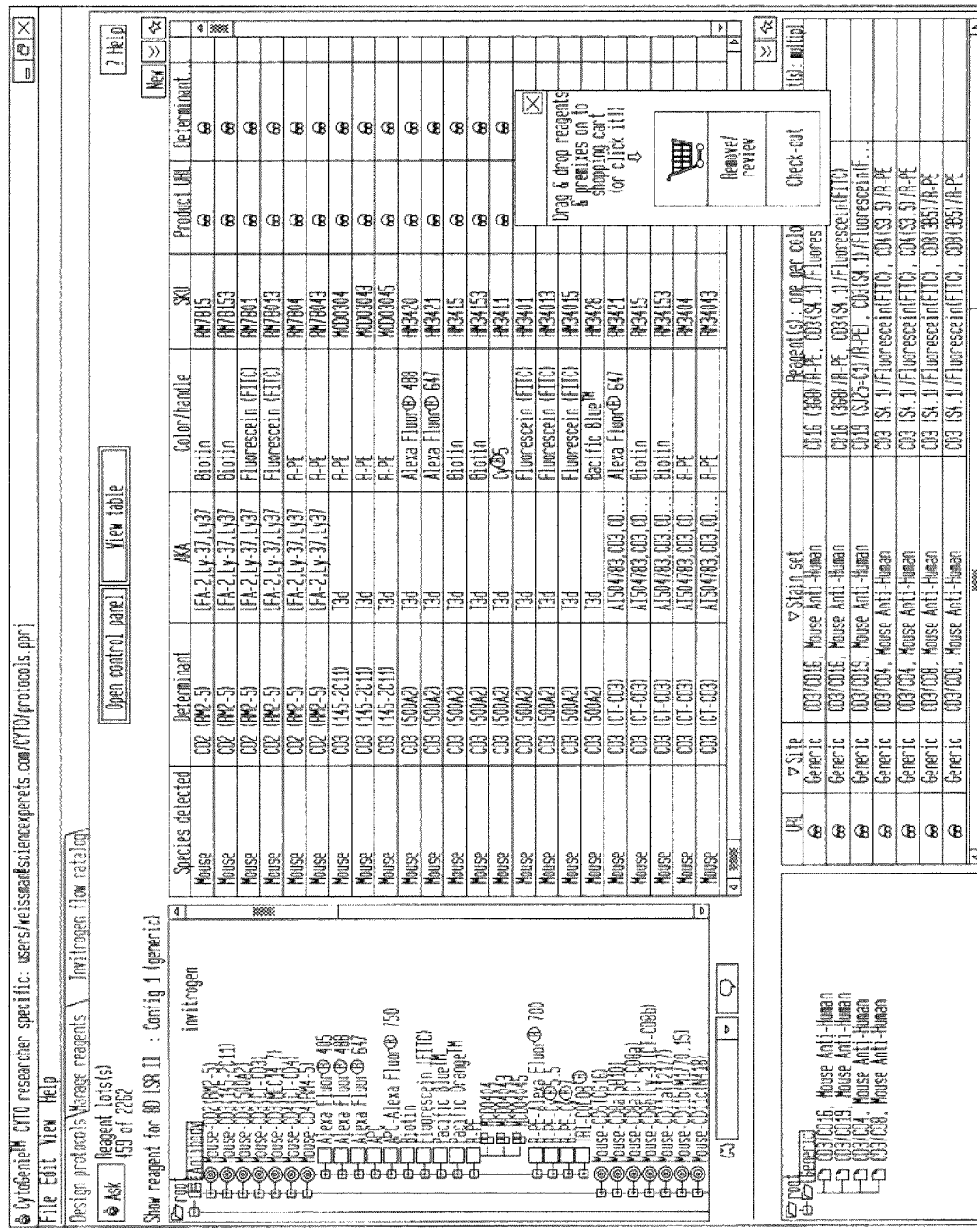
FIG. 1 shows a screencap of an embodiment of the system of the invention, with a navigation tree on the left hand side, and a table on the right hand side.

The term "activation marker" as used herein refers to an intracellular or cell surface marker that is highly associated with a particular cell and is selectively upregulated during a physiological condition. The physiological condition may be exposure to a substance, an allergen, a drug, a protein or a chemical, or other stimuli, or removal of a stimuli, a substance, a protein, an allergen, a drug or a chemical.

The term "antigen" and its various grammatical forms refers to any substance that can stimulate the production of antibodies and/or can combine specifically with them. The term "antigenic determinant" or "epitope" as used herein refers to an antigenic site on a molecule.

The term "cell surface marker" as used herein refers to an antigenic determinant or epitope found on the surface of a specific type of cell. Cell surface markers can facilitate the characterization of a cell type, its identification, and its isolation. Cell sorting techniques are based on cellular biomarkers where a cell surface marker(s) may be used for either positive selection or negative selection, i.e., for inclusion or exclusion, from a cell population.

The term "ChiSq value" as used herein refers to unnormalized values that are proportional to actual chi-square values and are calculated from the deviations of the measured event from the fit line in each of the spectral overlap fluorescences.

The term "chromophore" as used herein refers to a part (or moiety) of a molecule responsible for its color. The term "color" as used herein refers to the quality of an object or substance with respect to light reflected or absorbed by the object or substance. The three characteristics of color are hue, intensity, and value. "Hue" refers to a gradation, tint, or variety of a color. "Intensity", "chroma", and "saturation" are used interchangeably to refer to the strength or sharpness of a color. A color is full in intensity only when pure and unmixed. "Value" refers to a degree of lightness or darkness in a color. A chromophore is a region in a molecule where the energy difference between two different molecular orbitals falls within the range of the visible spectrum. Visible light that hits the chromophore thus can be absorbed by exciting an electron from its ground state into an excited state. In biological molecules that serve to capture or detect light energy, the chromophore is the moiety that causes a conformational change of the molecule when hit by light.

The term "compensation" as used herein refers to correction of an emission signal to accurately estimate the fluorescence signal for a given fluorophore.

Antigen-antibody interactions show a high degree of specificity, which is manifest at many levels. Brought down to the molecular level, specificity means that the combining sites of antibodies to an antigen have a complementarity different from the antigenic determinants of an unrelated antigen. The term "Cross-reactivity" as used herein refers to situations in which antigenic determinants of two different antigens have some structural similarity, as a result of which some degree of fitting of one determinant into the combining site of some antibodies to the other may occur.

The term "cytometry" as used herein refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and to collect cells (or other small particles) with measured characteristics that fall within a user-selected range of values.

As used herein, the term "data file" refers to an electronic collection of data that may be organized into columns and rows. As used herein, the term "data repository" refers to a collection of data files. Examples of a data repository include, but are not limited to, a database, a knowledge base, a text file, a spreadsheet, a table, a matrix, a group of image files, and the like.

The term "detector pass band" as used herein refers to an optical filter component of a detector of a flow cytometer located in the light path of incident light towards a detector.

The term "differential label" as used herein generally refers to a stain, dye, marker, antibody or antibody-dye combination, or intrinsically fluorescent cell-associated molecule, used to characterize or contrast components, small molecules, macromolecules, e.g., proteins, and other structures of a single cell or organism.

The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, and derivatives thereof.

The term "excitation" as used herein may be represented by Equation 1:

$$S_0 + h\nu \rightarrow S_1 \qquad \text{Equation [1]}$$

where h=Planck's constant and v=frequency of light. A photon of energy ($h\nu_{EX}$) supplied by an external source, such as a laser or a lamp, is absorbed by the fluorophore creating an excited electronic singlet state ($S_1'$). State $S_0$ is the ground state of the fluorophore and $S_1$ is its first (electronically) excited state. The excited state exists for a finite time during which the fluorophore (i) undergoes conformational changes and (ii) also is subject to a multitude of possible interactions with its molecular environment. These processes have two important consequences: 1) the energy of $S_1'$ is partially dissipated, yielding a relaxed singlet excited state ($S_1$) from which fluorescence emission originates; and 2) not all the molecules initially excited by absorption return to the ground state ($S_0$) by fluorescence emission. Other processes, such as, but not limited to, collisional quenching or fluorescent resonance energy transfer (FRET), also may depopulate $S_1$.

Molecules in an excited state ($S_1$) can relax by various competing pathways. They can undergo 'non-radiative relaxation' in which the excitation energy is dissipated as heat (vibrations) to the solvent. Excited organic molecules also can relax via conversion to a triplet state which subsequently may relax via phosphorescence or by a secondary non-radiative relaxation step. The term "relax" as used herein refers to the energy loss of an excited molecule. Relaxation of an $S_1$ state also can occur through fluorescence quenching by interaction with a second molecule. The fluorescence quantum yield, which is the ratio of the number of fluorescence photons emitted to the number of photons absorbed, is a measure of the relative extent to which these processes occur.

The term "emission" as used herein may be represented by Equation 2:

$$S_1 \rightarrow S_0 + h\nu \qquad \text{Equation [2]}$$

where h=Planck's constant and v=frequency of light. A photon of energy ($h\nu_{EM}$) is emitted, returning the fluorophore to its ground state ($S_0$). Due to energy dissipation during the excited-state lifetime, the energy of this photon is lower, and therefore of longer wavelength, than the excitation photon ($h\nu_{EX}$). The difference in energy or wavelength represented by ($h\nu_{EX} - h\nu_{EM}$) is the Stokes shift. The Stokes shift allows emission photons to be detected against a low background, isolated from excitation photons.

The specific frequencies of exciting and emitted light are dependent on the particular system. The entire fluorescence process is cyclical. A single fluorophore may generate thousands of detectable photons. For polyatomic molecules in solution, the discrete electronic transitions represented by $h\nu_{EX} - h\nu_{EM}$ are replaced by rather broad energy spectra called the fluorescence excitation spectrum and the fluorescence emission spectrum, respectively. Generally, the fluorescence excitation spectrum of a single fluorophore species in dilute solution is identical to its absorption spectrum. Under the same conditions, the fluorescence emission spectrum is independent of the excitation wavelength, due to the partial dissipation of excitation energy during the excited-state lifetime. The emission intensity is proportional to the amplitude of the fluorescence excitation spectrum at the excitation wavelength.

The term "excitation maximum" (singular of excitation maxima) as used herein, refers to the specific wavelength for each fluorescent dye that most effectively induces fluorescence.

The term "fluorescence" as used herein refers to the result of a three-state process that occurs in certain molecules, generally referred to as "fluorophores" or "fluorescent dyes," when a molecule or nanostructure relaxes to its ground state after being electrically excited. Stage 1 involves the excitation of a fluorophore through the absorption of light energy; Stage 2 involves a transient excited lifetime with some loss of energy; and Stage 3 involves the return of the fluorophore to its ground state accompanied by the emission of light.

The term "fluorescence compensation" as used herein refers to the process of transforming multicolor fluorescence measurements to yield estimates of the amount of each of the different dyes present. Generally, this requires evaluating the amount of signal each dye produces in each individual detector used to obtain the multicolor fluorescence measurement.

The term "fluorescent-activated cell sorting" (also referred to as "FACS"), as used herein refers to a method for sorting a heterogeneous mixture of biological cells into one or more containers, one cell at a time, based upon the specific light scattering and fluorescent characteristics of each cell.

The term "intracellular marker" as used herein refers to an antigenic or other determinant or epitope found inside a specific type of cell. Intracellular markers can facilitate the characterization of a cell type, its identification, and its isolation. Cell sorting techniques are based on cellular biomarkers where intracellular marker(s) may be used for either positive selection or negative selection, i.e., for inclusion or exclusion, from a cell population. Some intracellular markers can be detected in viable cells. Such markers include mitochondrial status or intracellular levels of a metabolite such as glutathione. Some intracellular markers can only be detected by disrupting the integrity of the cell surface membranes. These include markers that reveal the phosphorylation status of intracellular enzymes.

The term "surface marker" as used herein refers to markers that are distinguished from intracellular markers because they are located on the outer surface of the cell rather than inside the cell. Surface markers and intracellular markers can be detected on the same cell. Much the same methodology can be used to detect either type of marker, except that detection of some intracellular markers may require disruption of the cell membrane integrity and hence loss of viability for the cell.

Any cellular constituent may be used as a marker (surface or intracellular) as long as detection methods can be found to distinguish (differentiate) the marker from other cellular constituents.

The term "key word" as used herein refers to a significant or descriptive word used as a reference point for finding other words or information.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The terms "measurement channel" and "detector" are used interchangeably herein to refer to a component of a flow cytometer used to measure light.

The term "parameter" as used herein refers to a reference, value, or variable that refers to one of the pieces of data provided as input to a function, procedure, protocol, command, or program.

The term "peak excitation" as used herein refers to the wavelength at the maximum of an excitation peak. The wavelength at the maximum of the excitation peak is the wavelength which induces the maximum excitation of a fluorophore.

The term "pigment" as used herein refers to a material that changes the color of reflected or transmitted light as the result of wavelength-selective absorption.

The term "reactivity" as used herein refers to the relative capacity of an atom, molecule, or radical to undergo a chemical reaction with another atom, molecule, or compound.

As used herein, the term "spectrum" (singular of "spectra") refers to a range of light waves ordered in accordance with the magnitudes of their wavelengths. The term "emission spectrum" as used herein refers to the range of wavelengths within which a fluorophore emits light. Excitation and emission spectra of many dyes have been extensively studied. One skilled in the art will recognize that spectra may be obtained from the existing literature, or alternately, be determined via experimentation using various instrumentation such as, but not limited to, flow cytometers, fluorometers or spectrofluorometers.

As used herein, the term "spectral overlap" refers to two or more light spectra with at least one common wavelength.

The term "reagent" as used herein refers to a substance used in a chemical reaction to detect, measure, examine, or produce other substances. Reagents include, but are not limited to, a dye, an antibody, a fluorophores, and a chromophore.

The term "stain" as used herein refers to a composition of a dye(s) or pigment(s) used to make a structure, a material, a cell, a cell component, a membrane, a granule, a nucleus, a cell surface receptor, a peptide, a microorganism, a nucleic acid, a protein or a tissue distinguishable. The term "staining reagent" and, unless otherwise defined, the term "reagent" as used herein are synonymous with the term "stain."

The term "stain set" as used herein refers to a combination of stains. The terms "reagent combination" and "multiparameter stain set" as used herein are synonymous with the term "stain set." The term "marker" as used herein refers to a structure that is associated with a cell or particle and is detectable because it emits a signal including, but not limited to, fluorescence, that can be measured by a detection instrument or because it is reactive with a reagent that emits such a signal or causes the emission of such a signal.

The term "single stained" control or single stained sample as used herein refers to cells or particles whose fluorescence derives from a single stain, reagent, dye, or pigment.

The "unstained control" as used herein refers to cells or particles that are not known to have fluorescence derived from a stain, reagent, dye, or pigment.

The term "fluorescence minus one" (FMO) control as used herein refers to stain sets constructed to measure all of the markers detected by a given stain set except for one, which is omitted to enable determination of the exact fluorescence range of cells stained with all but the omitted stain.

The described invention provides methods for determining the effective spectrum matrix used in a flow cytometer, to methods for automating fluorescence compensation where fluorescence measurements for multiple fluorescence emitters are made on a series of single objects, to customizable, personalizable and automatable systems; and to methods for selecting and/or optimizing the selection of reagent combinations for the identification and/or quantification of molecules in or on cells, wherein the presence or amount of such molecules may be detected wholly or in part by methods that rely on coordinated fluorescence measurements or other properties of an instrument-measurable atom or molecule associated with the reagent combination. The invention also relates to automated methods for the selection of individual reagents and combinations of reagents necessary to provide "control" data to enable interpretation of the measurements. The invention also relates to automated personalizable methods for the location and purchase of individual reagents available from commercial sources and to the importation of information about such reagents into automatable methods for placing and maintaining reagent and sample information in close long-term association with primary and derived data collected pursuant to reaction of reagent(s) with sample(s).

The present invention is described below with reference to block diagrams and operational illustrations of methods and devices to select and present media related to a specific topic. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks.

1. System and Method for Selecting and Optimizing Fluorescent Reagent Combinations in Multiparameter Stain Sets According to one aspect, the described invention provides a system and method of use thereof that can operate interactively with a user to facilitate and automate performance of a series of tasks that may include at least one of (a) the design protocol for a flow cytometry assay, including, but not limited to, the design and selection of multiparameter stain sets, (b) the collection of data for an assay executed according to the protocol, and (c) the analysis of the collected data to extract findings that motivated the performance of the assay.

According to one embodiment, the design protocol for a flow cytometry assay can include at least one of the following:

(1) Protocol summary information entry: the system displays a protocol summary page on which the user may enter the name and other descriptive information and comments about the experiment;

(2) Subject, sample, and keyword information entry: the system displays a subject/sample page on which the user may enter subject names, sample names and keyword values or select these from previously entered values, and on which the user may enter text, drag and drop or point and click to create a table joining and displaying the appropriate subject, sample and keyword values;

(3) Stain set construction: the system displays a stain set entry page on which the user may perform the listed actions:

(i) Choose the data collection instrument: the user can interactively point and click or drag and drop to complete the required selection of at least one data collection instrument whose pre-entered capabilities will define the limits of reagents that can be included in stain sets in the current protocol;

(ii) Enter markers to be detected by a stain set and/or select reagents to include in a stain set: the user can interactively enter or choose the reagents to be included in at least one stain set, the markers to be detected in at least one stain set or a combination of both reagents and markers, the choice being accomplished by using text entry, point and click, or drag and drop capabilities to address a tree-structured marker/reagent display to perform at least one of the following actions for each desired marker/reagent:

(a) select a marker by name from the first level (after the root) of the tree;

(b) select an antibody or other marker detector from the second level of the tree;

(c) select a dye conjugate for a marker detector or an unconjugated detector from the third level of the tree;

(d) select a specific lot of a conjugated or unconjugated detector from the fourth level of the tree.

The users can repeat the above selection steps until all of the channels of the data collection instrument system have been filled. As each selection is made, the system uses the first column of a table shown in a panel to the right of the marker-reagent tree to display the marker(s) that have thus far been selected (either directly or via a lower level selection).

Alternatively, or in addition, with or without displaying the tree structure, the user can interactively enter or choose one or more markers to be detected by at least one stain set (auto-color option) by entering desired marker names or selecting markers from a selection widget available on each row of a table-like structure in the column that displays markers already selected by any method. The user can switch between entry modes without losing previous entries for the stain set, whether selected from the tree structure or entered directly into the column displaying desired markers.

(iii) Entry of expected properties for stain set targets (expected marker expression on cell or particle types in the cell/particle suspension that will be stained with the stain set): in response to a user keyboard or mouse click on an "add target" button, (a) the system may provide a dropdown or otherwise convey a list of previously added cell/particle types and may provide a method to enable addition of new targets to the list. For each cell/particle type selected from the list, the system may add a marker expression level input column in which each cell may contain previously entered information for the marker in/on the cell/particle specified by the column and/or provide access to a dropdown or other selectable display of expression levels from which the user can choose.

(b) the system may additionally provide an "options" dropdown and/or provide other methods whereby the user can select one or more options that may identify intended cell/particle pre-treatment or staining protocol conditions that may influence the reagent choice for detection of all, or just some, of the markers selected for stain set detection. If the selected option(s) require reagent choice decisions that are applicable to all markers detected by the stain set, the system may directly convey the option choice to the stain set defining module(s). If the selected option requires user input to enable the system to make reagent choice actions that may differ between individual markers, the selection of such options may trigger the system to add columns that may have dropdowns or other methods through which the use can add/select or otherwise input the needed information. In all cases, if the marker expression level for the selected target cell/particle has already been entered or is otherwise known to the system, the system may automatically display the known value for the target and may allow replacement with a different expression level if the user so specifics.

(iv) Computation and ranking of possible stain sets: when the above information entry is complete, the user can trigger the system to compute a rank-ordered list of feasible stain sets that:

(a) satisfy the user's marker/reagent choices;

(b) fit within the fluorescence spectral detection and other limitations defined by the user's data collection instrument choice;

(c) fit with the limitations imposed by the treatment of the sample either prior to, or during the staining procedure;

(d) can be constructed, according to user specification, from reagents known to the system as being one or more of the following:

(i) currently available in the local inventory available to the user;

(ii) listed in the local inventory but currently not available (for example, but not limited to, temporarily out of stock);

(iii) listed in the system knowledge store as available from commercial sources;

(iv) known to the system via any information source that system can access via the internet.

The system displays this list of feasible stain sets ranked according to how well each stain set is likely to discriminate cells/particles with the expression level properties indicated by the user. To rank the list, a score is assigned to each reagent combination based on properties that may include: the expected presence and expression level of markers on the same cell/particle as indicated by the user or otherwise known to the system, the potential spectral overlap of the dyes associated with the reagents that react with those markers, the exclusion of spectral overlap consideration for dyes in "dump" channels (which will exclude cells detected by reagents assigned to these channels); the likelihood that primary or "second step" anti-immunoglobulin reagents will cause interference; the likelihood that fluorescence signals from markers or fluorescent reagents detecting markers will be compromised by permeabilization or other treatment(s) of the cells or particles prior to, during, or after a given staining step; the fixation or other state-defining treatments of particles/cells prior to or during staining that restrict the choice of surface or intracellular reagents and fluorochromes; the quality of the reagent itself (entered as a reagent property in the reagent record); and the local availability of the reagent, which can be specified as a restriction by the user.

In considering feasible stain sets, the system takes into account sensitivity to staining conditions that influence some dyes (and not others) and rules sensitive stains out of the stain step where they might be used. Where possible, it moves the use of such dyes to a step in the staining procedure where the staining conditions will not interfere with efficacy with which the dye is detected. In addition, the system takes into account determinant (aka marker) sensitivity to staining conditions that influence the detectability of such determinants and limits use of reagents to detect such determinants to stain step(s) at which detection of the determinant(s) is not expected to be compromised. For example, the system takes into account treatments that occur before staining, including, but not limited to, fixation of the cells, viable incubation of the cells with drugs, or other treatments that change the cells prior to staining. The system also takes into account treatments that occur during staining procedures (e.g., methanol fixation between the first staining step and the second staining step). The system further takes into account treatments that occur after staining, including, but not limited to, fixations or other treatments that influence the staining levels of the cells by influencing levels of expression or availability of determinants to which reagents have bound, the ability of the determinants or cells to retain intracellular or bound antibody or other stains, the fluorescence emission of the dyes, or the autofluorescence levels of the cells (e.g., paraformaldehyde fixation).

When computation is complete, the system displays the ranked stain set list in a table in which each row shows the stain set rank, the score assigned to the stain set (an indication of its likelihood of discriminating the user-identified cells/particles), and the reagents contained in the stain set. In addition, each row contain a selection "box" that enables the user to choose the stain set for inclusion in the group of stain sets available for use in a current protocol.

The system may permanently record a stain set that is constructed and may enable recall of previous stain sets. The system may also enable copying and editing of recalled stain sets for editing and/or re-use in subsequent experiments. The system may automatically test recalled stain sets for compatibility with current samples and instrumentation and may suggest, enable or automatically implement re-optimization of the stain set composition to accord with current conditions.

(4) Combination of samples and stain sets: the system may display a page on which the stain sets the user has chosen/constructed and the samples to be stained with the stain sets are combined such that each sample is stained with each stain set. The user can eliminate any non-desired sample/stain set combinations or preselect reagents and samples to combine to create the final assay list.

(5) Inclusion of controls: The system next inspects the remaining combinations and develops a set of controls based on the need for single stain fluorescence compensation samples for the dyes used in the assay, and the need for FMO controls for sample/stain set combinations where the expected marker expression levels indicate that fluorescence overlap may be a problem with a particular reagent combination. The list of single stain controls is constructed based on knowledge of which dyes require a control for each reagent-dye conjugate and the dyes that require one control even when different reagents are used with the dye. Unstained controls are added where necessary to complete the compensation control list.

(6) Construction of pipetting layout: In some embodiments, the system next displays the stain set—sample combinations and the control sample list in a "plate-rack" layout that provides a plan for executing the experiment. The user can adjust various aspects of this plan according to taste. The system then uses reagent dilutions and other user entered values to compute the amounts of each stain set and sample to be added to the tube or other staining vessel, the amounts of each reagent and the diluent needed to construct each stain set, and ultimately the amounts of all reagents and stain sets needed to execute the experiment. In some embodiments, the system creates dilution series for specified reagents, calculates needed amounts, and constructs the pipetting plan for the series.

(7) Printing, recording, and exporting the protocol: Once the plate-rack plan is complete and the reagent and sample volumes computed, in some embodiments, the system provides utilities that allow the user to selectively print some or all aspects of the protocol and to create and export machine-readable protocol output files for storage and for passage to data collection instruments.

According to another aspect, the described invention provides systems and methods for defining the reagents that comprise a stain set (reagent combination) to identify or quantitate molecules (markers) in or on cells, surfaces, liquids, or solids, with or without user reference to at least one property of at least one instrument-measurable atom or molecule associated with the reagent combination.

According to one embodiment, the described invention provides a method for selecting a reagent combination for the identification and quantification of at least one molecule in or on cells with or without reference to at least one property of at least one instrument-measurable atom or molecule associated, either directly or indirectly, with the reagent combination, the method comprising: (a) specifying a plurality of markers (parameters) to be detected by a plurality of reagents; (b) optionally specifying at least one expected level of expression of one or more markers in a plurality of markers expected to be detected on or in each of a plurality of cells; (c) generating a plurality of reagent combinations comprising a plurality of reagents to detect the plurality of markers of step (a), wherein the reagent combinations are ranked according to at least one user-defined or system-defined criterion; and (d) providing a rank-ordered list of combinations.

According to some embodiments, at least one of steps (a), (b), (c) and (d) is performed manually. According to some embodiments, at least one of steps (a), (b), (c) and (d) is performed automatically. According to some embodiments, at least one of steps (a), (b), (c) and (d) is performed using a computer to identify some or all reagents or stain sets used for staining the cells or particles for which data were collected in a previously collected data set. According to some embodiments, the expected level of expression of at least one marker(s) on at least one cell type to be targeted by a stain set being developed can be arbitrarily selected manually from a list of expression levels displayed by a computer.

According to some embodiments, at least one of steps (a), (b), (c), and (d) is performed using a computer (i) to identify at least one subset of cells or particles for which data were collected in a previously collected data set; (i) to create a list containing at least one of the reagents used to stain used for staining at least one subset of cells or particles for which data were collected in a previously collected data set; (iii) to extract derived quantitative data such as median fluorescence as an index of reagent staining capability for at least one subset; (iv) to associate at least one of the reagents on said list with the level of the marker it detects on at least one subset detectable in previously collected data; and (v) to use this association to specify the expected level of expression for the marker during stain set development.

According to some embodiments, at least one of steps (a), (b), (c), and (d) and at least one of steps (d i-v) is performed using a computer to perform automated cluster analysis that identifies at least one subset according to the expression of at least one of a plurality of cell surface markers, extracts marker expression level data for the identified subset(s), and makes this data available or directly transfers it so that it can be used to define the expected level(s) of marker expression or other characteristics that influence marker detection on at least one subset to be detected by the stain set under development.

According to another embodiment, at least one molecule is an activation marker. According to another embodiment, at least one molecule is an antigen. According to another embodiment, at least one molecule is a cell surface marker. According to another embodiment, at least one molecule is an intracellular marker. According to another embodiment, at least one molecule is a chromophore. According to another embodiment, at least one molecule is a differential label. According to another embodiment, at least one molecule is a dye. According to another embodiment, at least one molecule is a stain.

According to another embodiment, at least one instrument-measurable atom, molecule or molecular complex is an antigen. According to another embodiment, at least one instrument-measurable, molecule or molecular complex is an activation marker. According to another embodiment, at least one instrument-measurable atom, molecule or molecular complex is a cell surface marker. According to another embodiment, at least one atom, molecule or molecular complex is an intracellular marker. According to another embodiment, at least one instrument-measurable atom, molecule or molecular complex is a chromophore. According to another embodiment, at least one instrument-measurable atom, molecule or molecular complex is a differential label. According to another embodiment, at least one instrument-measurable, molecule or molecular complex is a dye. According to another embodiment, at least one instrument-measurable atom, molecule or molecular complex is a stain.

According to one embodiment, step (a) further comprises the step of specifying a plurality of reagents that can detect, directly or indirectly, at least one marker. According to some such embodiments, detection is qualitative, i.e., the presence of the molecule is perceived. According to some such embodiments, detection is quantitative, i.e., the amount of signal generated by the chromophore or other signal source is measured. According to some such embodiments, the specifying step is performed using a computer. According to another embodiment, step (a) further comprises the step of specifying the instrument-measurable atom/molecule associated with each of the plurality of reagents. According to some such embodiments, the specifying step is performed using a computer.

According to another embodiment, step (a) further comprises the steps of (i) specifying a plurality of measurement instruments and (ii) specifying at least one property of at least one measurement capability of at least one measurement instrument. According to some such embodiments, at least one of these specifying steps is performed using a computer.

According to some such embodiments, the measurement instrument is a flow cytometer. According to some such embodiments, the measurement instrument is a fluorescence microscope. According to some such embodiments, the measurement instrument is a fluorometer. According to some such embodiments, the measurement instrument is a spectrofluorometer. According to some such embodiments, the measurement instrument is a microarray scanner. According to some such embodiments, the measurement instrument is a microtiter plate scanner.

According to some embodiments, at least one fluorescence measurement may be associated with a reagent or molecule that may be used to indicate the relative or absolute amount of a sample that is accessible to the measurement instrument. According to some such embodiments, a known quantity of the fluorescent reagent or molecule to be included for this purpose may be added to a known volume of the sample prior to measurement or dispersal for measurement. In some such embodiments, the fluorescent reagent or molecule may be added to a sample that will be distributed as "spots" on a microarray. In some such embodiments, the fluorescent reagent or molecule may be added to a sample prior to distributing the sample into one or more wells in a microtiter plate. In some such embodiments, the fluorescent reagent or molecule may be added to a sample prior to distribution onto microscope slides. According to some such embodiments, the reagent or molecule may be associated with, or covalently bonded to, a macromolecule or a particulate. According to some such embodiments, the fluorescent reagent or molecule may be formulated with the sample in known proportions.

According to some such embodiments, the relative or absolute amount of the added reagents may be computed after fluorescence compensation corrections have been applied.

According to one embodiment, step (d) further comprises the step of selecting a reagent combination.

According to another embodiment, step (a) is based upon information from a genomic analysis. According to some such embodiments, information from a genomic analysis includes, but is not limited to, a level of expression of a cell surface marker, and a level of expression of an activation marker.

According to another embodiment, the user-defined criterion or system-defined criterion is a spectral interaction. According to some such embodiments, the spectral interaction is the range of the excitation maximum of a reagent of the reagent combination. According to some such embodiments, the spectral interaction is the range of the emission spectrum of a reagent of the reagent combination. According to some such embodiments, the spectral interaction is the range of spectral overlap of at least one reagent of the reagent combination with that of at least one other reagent of the reagent combination. According to some such embodiments, the spectral interaction is the excitation maximum of at least one reagent of the reagent combination.

According to another embodiment, the user-defined criterion or system-defined criterion is the ability of the measurement channels on an instrument to collectively detect and to individually discriminate each of the fluorescences emitted by the sources in the stain set. According to some embodiments, the user-defined criterion or system-defined criterion is the presence of a measurement channel with particular illumination and detection properties on an instrument.

According to some embodiments, the user-defined criterion or system-defined criterion is a detector filtered by a filter with a particular band pass capability.

According to another embodiment, the user-defined criterion or system-defined criterion is an illumination source on an instrument. According to some such embodiments, the illumination source is a laser excitation source. Laser excitation sources provide wavelength peaks that are well-defined, selective, and of high intensity, allowing more selective illumination of the sample. The best performance is achieved when the dye's peak excitation wavelength is close to the wavelength of the laser. Several lasers commonly used include, for example, the compact violet 405 nm laser, 488 nm blue-green argon-ion laser, 543 nm helium-neon green laser, and 633 nm helium-neon red laser. Mixed-gas lasers such as, for example, the krypton-argon laser, can output multiple laser lines which may require optical filters to achieve selective excitation. High-output light-emitting diodes (LEDs) provide selective wavelengths, low cost and energy consumption, and long lifetime. Single-color LEDs are ideal for low-cost instrumentation where they can be combined with simple long pass filters that block the LED excitation and allows the transmission of the dye signal. However, the range of wavelengths emitted from each LED still is relatively broad and also may require the use of a filter to narrow the bandwidth.

According to some embodiments, the user-defined criterion or system-defined criterion is the availability of a reagent of the reagent combination. The term "availability" as used herein refers to the quality of being or becoming at hand when needed, and includes, but is not limited to, the following conditions or any combination thereof: (a) the reagent is present in a collection of reagents; (b) the user has permission to use the reagent that is present in the collection; (c) the required amount of the regent is present and available in the collection. According to some such embodiments, the availability of the reagent is the availability of the reagent on-hand. According to some such embodiments, the availability of the reagent is the availability of the reagent from a second source. According to some such embodiments, the availability of the reagent is the availability of the reagent from a commercial vendor.

Figure 2:
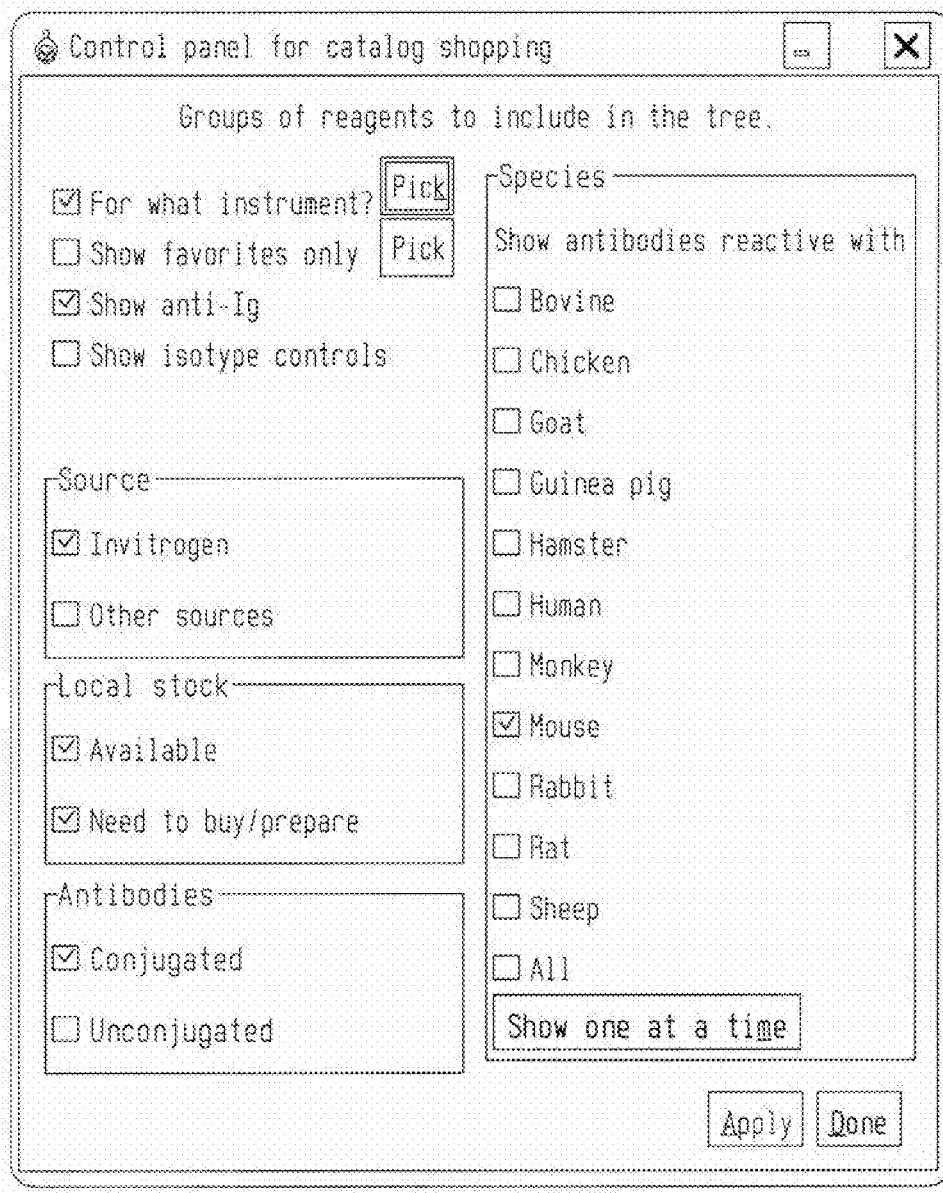
FIG. 2 shows a screencap of a window of the customizable search interface that facilitates the population of the navigation tree, the creation of tabs, and searches.

According to some embodiments, the availability of the reagent is the accessibility of information about the reagent necessary to determine its compatibility with other reagents in the combination, such as, but not limited to, the species derivation or the heavy and light chain composition of an antibody reagent. FIG. 2 shows a screencap of a window of the customizable search interface that facilitates the population of the navigation tree, the creation of tabs, and searches.

According to some such embodiments, the reagent data is maintained in a repository that includes a customizable first table and a customizable navigation tree, each of which may contain information, such that the display shows the user only the rows or nodes in which the user is interested. FIG. 1 shows a screencap of the system of one embodiment of the invention, with a navigation tree on the left hand side, and a table on the right hand side.

According to some such embodiments, the reagent data repository includes items in an inventory as well as data related to or pertaining to those inventoried items, including, but not limited to: reagent specificity information; reagent fluorescence information; reagent composition information; cell surface marker information; URL links to sources of reagent combinations or ingredients for forming reagent combinations; and the like.

According to some embodiments, users may view the reagent information in the reagent repository and manually select at least one reagent to include in a stain set. According to some embodiments, the information in the reagent data repository may be displayed in a table whose rows are assigned to individual reagents or reagent lots and whose columns contain properties of the reagents listed in the rows. According to some embodiments, the table may be converted to a "tree table" in which information in some columns is displayed as hierarchical nodes in a tree while information in other columns is maintained in table (row/column) format. According to some embodiments, columns whose contents are depicted as nodes in the hierarchical tree can be placed in the tree in any order. According to some embodiments, the tree nodes remain connected to the table such that selecting a node also selects the table rows that are encompassed by the node.

Figure 3:
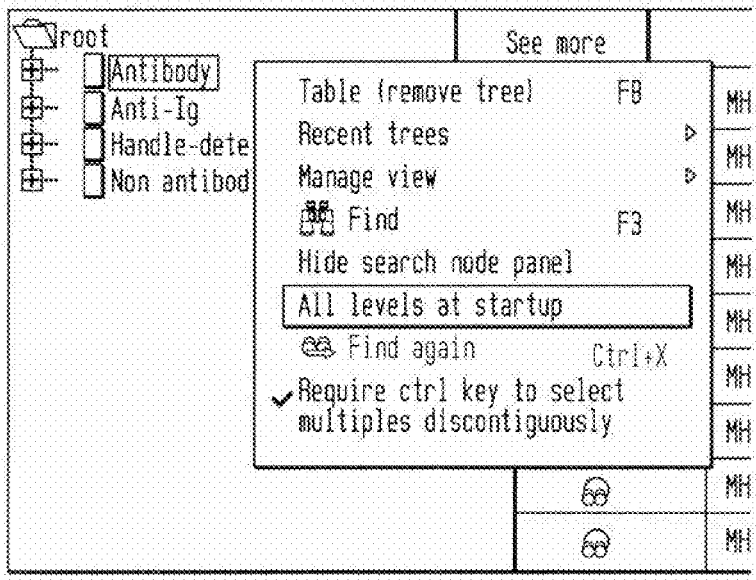
FIG. 3 shows a screencap of the options available when right-clicking over a node of the navigation tree.

According to some such embodiments, at least one node may be created for each data cell containing data in at least one column. According to some such embodiments, a user may create nodes manually for the purpose of navigating the tree. According to some such embodiments, at least one node is in at least one level of the navigation tree. Typically, a navigation tree has several levels; the first level typically is called the root, and subsequent levels are denoted by nodes. FIG. 3 shows a screencap of the options available when right-clicking over a node of the navigation tree. FIG. 4 shows a screencap of the options available when right-clicking over a node of the navigation tree. FIG. 5 shows a screencap of a window of the customizable search interface that facilitates population of the navigation tree, the creation of tabs, and searches. For example, a navigation tree displaying the contents of an operating system would have the main hard drive as the root, and folders located on the main hard drive as the nodes on the second level. The sub-folders located within the nodes on the second level would create nodes on a third level under each applicable second level node, and so on.

According to some such embodiments, the display order of at least two or more nodes in the navigation tree may be customized. According to some such embodiments, at least one node may be expanded or contracted upon selection.

According to some such embodiments, at least one tab may be created from the data in at least one data cell from at least one column. In some such embodiments, a table has a plurality of columns. In one example, the data in one column is called "cell surface marker information." The table has a plurality of rows, such that at least one row is called "reagent information A" "and at least one row is called "reagent information B". In this example, "reagent information" A and B represent two entries of distinct data.

In some such embodiments, a tab is created for either or both of the distinct data entries, such that when selected, a tab created for "reagent information A" will display all information from the table that contains "reagent information A", and a tab created for "reagent information B" will display all information from the table that contains "reagent information B."

According to some embodiments, more than one tab is created from the distinct data entry values in a column. According to some such embodiments, all information in the column in the table that corresponds to the selected tab is displayed when a tab is selected.

Figure 6:
FIG. 6 shows a screencap of a window of the customizable search interface where a user can order products or information from the server.

According to some such embodiments, at least one data entry within a column is abbreviated by a user. FIG. 6 shows a screencap of a window of the customizable search interface where a user can order products or information from the server. The abbreviation automatically is created in a new abbreviation column based on generic row abbreviating logic. A user can have the option of specifying as to what each abbreviation refers by changing the abbreviation according to the user's own specifications. As a result, the abbreviation provides the user a way of viewing information in the table in shorthand. Key words also can be used to annotate rows in the table and thereby expand the columns. Thus, a user can define a particular key word/value pair in order to annotate one or more rows in the table.

According to some embodiments, the columns in the table can be converted in any order to the levels of a tree whose nodes correspond at each level to the information in the column for the level. According to some embodiments, all of the information in the columns not included in the tree is displayed when the tree root is selected and selected information in the columns is displayed according to the nodes selected in the tree.

In one implementation, the information in the table is defined by an external source such as a library or a merchant and cannot be edited by the user. In other implementations, the information is supplied wholly or in part by the user. In other implementations, the information is supplied wholly or in part by automated analyses of data from external sources. In editable implementations, the user can evoke utilities that guide the entry of information into the table or perform queries that load information from external sources. The user also can create a table column that facilies row identification by invoking a utility that operates on each table row to concatenate the contents of several columns in a specified order and to insert the concatenated string for each row in the column created for this purpose. With this utility, the user can specify whether the concatenated string contains the full contents of each of the specified columns, unique abbreviations generated automatically for the contents in each of the specified columns, or user-supplied aliases or abbreviations. The user also can edit or replace any of the concatenated entries.

According to one embodiment, the user uses the reagent information displayed in a "tree-table" to manually select at least one reagent from the reagent repository and to place that reagent in a stain set. According to one embodiment, the user-defined criterion for selection is the marker detected by the reagent.

According to another embodiment, the user-defined criterion or system-defined criterion for selection of at least one reagent for a stain set is based on a need or desire to define a stain set (reagent combination) that optimally detects at least one marker on at least one type of cell or particle. According to some such embodiments, the user-defined or system-defined criterion is a known reactivity of a reagent of a reagent combination. According to another embodiment, the user-defined criterion or system-defined criterion is a cross-reactivity of a reagent of a reagent combination. According to some embodiments, the user-defined criterion or system-defined criterion is the cost of a reagent in a reagent combination. According to some such embodiments, the cost is the total cost of the reagent combination. According to another embodiment, the user-defined criterion or system-defined criterion is an available analysis capability. As used herein, the term "available analysis capability" refers to the examining, detection or measuring abilities of an instrument.

According to another embodiment, the user-defined or system-defined criterion is the stability of a fluorescent reagent in solution or when distributed onto microscope slides, microarrays or other solid media. According to another embodiment, the user-defined or system-defined criterion is the stability of a fluorescent reagent under conditions where it exposed to light at wavelengths that excite it.

According to another embodiment, the user-defined or system-defined criterion is an interaction that may occur between reagents. According to another embodiment, the user-defined or system-defined criterion is the occurrence of energy transfer between reagents. According to another embodiment, the user-defined or system-defined criterion is a reaction leading to fluorescence quenching. According to another embodiment, the user-defined or system-defined criterion is a reaction leading to loss of reagent solubility. According to another embodiment, the interaction is directly between two or more fluorochromes. According to another embodiment, the interaction between or among fluorochromes is mediated via binding to macromolecules in the solution or on a solid substrate.

According to another embodiment, the at least one property is sensitivity of the marker to destruction by treatments such as, but not limited to, permeabilization, that occur prior to, during, or after a given staining step. According to another embodiment, at least one property is sensitivity of the fluorochrome to destruction by treatments such as, but not limited to, permeabilization, that occur prior to, during, or after a given staining step. According to another embodiment, at least one property is sensitivity of the fluorochrome to "bleaching" that occurs during laser excitation or other visualizations.

According to another embodiment, at least one property is fluorescence. According to another embodiment, at least one property is a dye spectrum. According to another embodiment, at least one property is a filter. According to another embodiment, at least one property is a spectral overlap detection capability.

According to another embodiment, generating of the plurality of reagent combinations step (c) further comprises the step of transmitting marker information based on a marker characteristic of at least one type of cell or particle to a reagent data repository. According to some such embodiments, the specifying and transmitting step is performed using a computer. According to another embodiment, generating of the plurality of reagent combinations step (c) further comprises the step of receiving reagent information from the data repository according to the transmitted marker information. According to some such embodiments, the specifying step is performed using a computer. According to another embodiment, generating of the plurality of reagent combinations step (c) further comprises the step of generating the plurality of reagent combinations according to the reagent information from the data repository. According to some such embodiments, the specifying step is performed using a computer.

According to another embodiment, reagent combinations are ranked automatically according to an efficacy of the reagent combination with regard to at least one type of cell, where efficacy criteria are selected automatically or manually and contain at least one criteria that include availability of reagents and the amount of spectral overlap in reagent-detector channels. According to another embodiment, the reagent combination is ranked manually according to user generated preferences. In some embodiments, the efficacy of the reagent combination is determined by a computer. In some embodiments, efficacy is considered optimal for at least one cell type when the amount of spectral overlap is computed to introduce minimal interference in the detection of at least one marker that is indicated as being expressed at low levels on a cell type of interest.

According to some such embodiments, the efficacy of a reagent combination with regard to at least one type of cell is determined by comparing a spectral overlap of a first reagent within the reagent combination with spectral overlap of a second reagent within the reagent combination. According to some such embodiments, the efficacy of the reagent combination with regard to at least one type of cell is determined by comparing a fluorescence excitation maximum for a first reagent of the reagent combination at a first wavelength with a fluorescence excitation maximum for a second reagent of the reagent combination at a second wavelength.

According to some such embodiments, the efficacy of the reagent combination with regards to at least one type of cell is determined by comparing a first amplitude of a first fluorescence emission spectrum of a reagent of the reagent combination to a second amplitude of a second fluorescence emission spectrum of a second reagent of the reagent combination. According to some such embodiments, the efficacy of the reagent combination with regard to the least one type of cell is determined by comparing a first spectral overlap of a first reagent of the reagent combination to a spectral overlap of a second reagent of the reagent combination. According to some such embodiments, the efficacy of the reagent combination with regard to at least one type of cell is determined by comparing a fluorescence excitation maximum for at least one reagent of the reagent combination to a fluorescence excitation maximum for at least one reagent of the reagent combination.

According to some such embodiments, the efficacy of the reagent combination with regard to at least one type of cell is determined by measuring autofluorescence of at least one type of cell. According to some such embodiments, the efficacy of the reagent combination with regard to at least one type of cell is determined by measuring an affinity of at least one reagent of the reagent combination for at least one type of cell. According to some such embodiments, the efficacy of the reagent combination with regard to at least one type of cell is determined by measuring fluorescence compensation required for each reagent of the reagent combination.

According to some such embodiments, the efficacy of the reagent combination with regard to at least one type of cell is determined by the ability to resolve low expression of at least one marker from levels of expression of said marker that fall below detectability thresholds. According to some such embodiments, the efficacy of the reagent combination with regard to at least one type of cell is determined by the ability to detect two or more markers expressed at levels that differ by 10-fold to 10,000-fold.

According to some such embodiments, the efficacy of the reagent combination with regard to at least one type of cell is determined from the total monetary cost of the reagent combination.

According to some such embodiments, the efficacy of the reagent combination with regard to at least one type of cell is determined from known reproducibility of results of the reagent combination.

According to another embodiment, the ranking step (b) identifies at least one type of cell or to segregate at least one type of cell from the population of cells.

According to some such embodiments, the ranking step (b) is performed manually according to user generated preferences. According to some such embodiments, the ranking step (b) is performed automatically according to a predetermined efficacy with regard to at least one type of cell.

According to some embodiments, the efficacy of the reagent combination with regard to at least one type of cell is determined from known interactions between reagents in the reagent combination.

According to some such embodiments, the efficacy of the reagent combination with regard to at least one type of cell is determined from known interactions between reagents in the reagent combination.

According to some such embodiments, the efficacy of the reagent combination with regard to at least one type of cell is determined from known interactions between reagents in the reagent combination.

According to some such embodiments, the ranking of the reagent combinations includes ranking the reagent combinations automatically according to a predetermined efficacy with regard to at least one type of cell. According to some such embodiments, the ranking of the reagent combinations includes ranking the reagent combinations manually according to user generated preferences.

According to some such embodiments, the efficacy of the reagent combination with regard to at least one type of cell is determined based on whether reagent availability or other user-determined or system-determined criteria force at least one of the reagents in the reagent combination to be detected via a fluorochrome-coupled "second-step" reagent.

According to some embodiments, the ranking of the reagent combinations may include determining whether an amount of each of the ingredients available for each reagent combination is sufficient is not sufficient, excluding reagent combinations for which the available quantity of any of the ingredients is insufficient, and ranking only the nonexcluded reagent combinations. An ingredient is determined to be insufficient if the amount of the ingredient that is available is less than the amount of the ingredient that is required for a particular reagent combination. An ingredient is determined to be sufficient if the amount of the ingredient that is available is equal to or greater than the amount of the ingredient required for a particular reagent combination.

According to some embodiments, the method further comprises: (i) using a "personal reagent shopper" that operates on a computer to search a data repository via a computer network to determine whether at least one ingredient for at least one of the reagent combinations is available from at least one supplier, and (ii) ordering a quantity of at least one ingredient from at least one supplier. According to some embodiments, the method further comprises the steps: (iii) assembling at least one reagent combination into a stain set comprising at least one of the reagent combinations and (iv) identifying the set of single-stain measurements needed in order to compute and apply compensation corrections for data collected with the stain set. According to some embodiments, the method further comprises identifying the FMO controls (stain sets lacking only a single reagent) necessary to define lower detection thresholds for reagents where compensation corrections may impair data interpretation for markers of interest. According to some embodiments, the method further comprises the inclusion of unstained cell samples for each stain set in which autofluorescence may impair interpretation of data for markers expressed in or near the autofluorescence range of particular cell types.

According to another embodiment, the user can use the personal reagent shopper to search the plurality of reagent combinations to find a particular reagent combination.

According to another embodiment, the optimal dye combination can be predicted. According to some such embodiments an amount of correction needed due to overlap of fluorescent dyes can be minimized by predicting the optimal dye combination.

According to some such embodiments, the generating of the experiment plan further comprises: (i) determining a dilution of the reagent combination, (ii) calculating a volume of the reagent combination, (iii) calculating a volume of a sample population of cells, and (iv) determining a quantity of at least one fluorescent dye for use in creating a multiparameter Hi-D stain set for flow cytometry or fluorescence microscopy.

According to some embodiments, the plurality of reagent combinations are ranked to identify at least one type of cell or to segregate at least one type of cell from a population of cells. According to some such embodiments, the ranking of the reagent combinations includes ranking the reagent combinations automatically according to a predetermined efficacy with regard to at least one type of cell. According to some such embodiments, the ranking of the reagent combinations includes ranking the reagent combinations manually according to user generated preferences.

According to some embodiments, the method further comprises using a "personal reagent shopper" to search a computer data repository via a computer network to determine whether at least one ingredient for at least one of the reagent combinations is available from at least one supplier. According to some embodiments, the method further comprises using a personal reagent shopper to "import" reagent descriptions from suppliers to enlarge the universe of reagents from which reagents for stain sets are manually or automatically drawn during the definition and/or optimization of stain sets. According to some embodiments, the method further comprises using a personal reagent shopper to order or cause to be ordered a quantity of at least one stain set ingredient from at least one supplier.

According to some embodiments the user can use a computer interface to manually instruct the personal reagent shopper to locate individual reagents or classes of reagents. According to some embodiments the user can use a computer interface to manually instruct the personal reagent shopper to locate reagents that detect individual markers. According to some embodiments the personal reagent shopper can be automatically instructed by a computer to locate individual reagents, classes of reagents, or reagents that detect individual markers. According to some embodiments, the said automatic instruction may be pursuant to the automatic definition of the reagents in a stain set. According to some embodiments, the said automatic instruction may be pursuant to the automatic optimization of a stain set.

According to some embodiments, the method further comprises the assembly of at least one previously defined reagent combination together with additional reagents or stain sets identified with by the personal reagent shopper in order to comprise a larger optimizable stain set.

According to another embodiment, the user can use the personal reagent shopper to search the plurality of already defined reagent combinations and/or commercially available reagent combinations to find at least pre-defined one reagent combination that contains at least one specified reagent. According to another embodiment, the user can use the shopper to search the plurality of already defined reagent combinations and/or commercially available reagent combinations to find at least one reagent combination that meets specified reagent availability conditions. According to another embodiment, the user can use the shopper search the plurality of already defined reagent combinations and/or commercially available reagent combinations to find a particular reagent combination that is compatible with detection by one or more instruments.

According to another embodiment, the optimal dye combinations can be predicted based on the properties of available reagent-dye conjugates and the detection properties of the data collection instrument. According to some such embodiments an amount of correction needed due to overlap of fluorescent dyes can be minimized by predicting the best dye combination.

According to one embodiment, the user is required only to specify the intended fluorescence detection instrument, and markers whose detection is desired. According to another embodiment, the user also is required to specify the expected amounts of at least one marker expressed on the cells or particles to be detected. According to another embodiment, the system returns to the user with a list of markers the user's available reagents can detect together with a list the "needed" markers, designated in an identifiable way, for which the system will have to "shop" for reagents to locate a source from reagent catalogs or other reagent lists available to the system. According to another embodiment, the user can select from the lists return by the system to inform the system as to which markers the system should eliminate and which the system should "shop" for. According to some embodiments, the system will "shop" for the needed reagents and return to the user with a completed stain set, or with a stain set marker as infeasible due to inaccessibility of feasible reagent combinations.

According to another aspect, the described invention provides a method for generating an experiment plan to collect multiparameter experiment data for the identification and/or quantification of at least one molecule in or on cells with or without reference to at least one property of at least one instrument-measurable atom or molecule associated, directly or indirectly, with the reagent combination, the method comprising (a) generating a plurality of reagent combinations each comprising a plurality of reagents to detect a plurality of markers, (b) specifying at least one level of expression of one or more markers in the plurality of markers expected to be detected on or in each of a plurality of cells; (c) generating a rank-ordered list of reagent combinations ranked according to at least one user-defined or system-defined criterion; and (d) determining an optimal reagent combination.

According to some embodiments, at least one of steps (a), (b), (c) and (d) is performed manually. According to some embodiments, at least one of steps (a), (b), (c) and (d) is performed automatically. According to some embodiments, at least one of steps (a), (b), (c), and (d) is performed using a computer.

According to another embodiment, generating a plurality of reagent combinations step (a) further comprises specifying a plurality of reagents that can detect or participate in the detection of one or more of the plurality of markers. According to some such embodiments, the specifying step is performed using a computer. According to another embodiment, generating a plurality of reagent combinations step (a) further comprises specifying at least one fluorescent dye or other instrument-measurable atom or molecule associated with each reagent. According to some such embodiments, the specifying step is performed using a computer. According to another embodiment, generating a plurality of reagent combinations step (a) further comprises specifying a plurality of measurement instruments and the properties or measurement capabilities of each. According to some such embodiments, the specifying step is performed using a computer.

According to another embodiment, at least one user-defined or system-defined criterion of step (c) is a spectral interaction. According to another embodiment, at least one user-defined or system-defined criterion of step (c) is at least one detector on an instrument. According to another embodiment, at least one user-defined or system-defined criterion of step (c) is at least one illumination source on an instrument. According to another embodiment, at least one user-defined or system-defined criterion of step (c) is the amount of reagent on-hand. According to another embodiment, at least one user-defined or system-defined criterion of step (c) is a known reactivity of at least one reagent in each reagent combination. According to another embodiment, at least one user-defined or system-defined criterion of step (c) is a known cross-reactivity of at least one reagent in each reagent combination. According to another embodiment, at least one user-defined or system-defined criterion of step (c) is at least one property of each reagent in each reagent combination. According to another embodiment, at least one user-defined or system-defined criterion of step (c) is an available analysis capability and species of an instrument.

According to another embodiment, the method further comprises the deployment of the stain sets in experiments. In some such embodiments, this deployment generates data that facilitates the development and optimization of new stain sets and/or the improvement and optimization of existing stain sets.

According to some such embodiments, the method further comprises generating an annotated experiment plan based on combination of at least one type of cell and at least one reagent combination, this to be accomplished by at least one of steps (a) pointing-and-clicking or dragging-and-dropping by means of a computer subjects, samples, and keywords for the experiment, (b) generating a ready-to-use pipetting plan based on automatic or user-defined combinations of subjects, samples, keywords and stain sets and, (c) printing the ready-to-use pipetting plan. According to some embodiments, a personal reagent shopper may be instructed either manually or automatically to locate one or more reagents necessary to construct and/or optimize stain sets intended for use in the experiment plan.

According to another embodiment, the method further comprises generating an annotated experiment plan based on combination of (i) at least one type of cell in at least one sample in the experiment and (ii) at least one optimized reagent combination, by using a computer to perform at least one of the following steps: (a) pointing-and-clicking or dragging-and-dropping by means of a computer to create a sample list containing at least one sample annotated with at least one of (i) sample identifier, (ii) subject or other name of sample source and (iii) keywords that (further) identify subjects or samples; (b) pointing-and-clicking or dragging-and-dropping by means of a computer to create a list stain sets (reagent combinations) for the experiment; (c) automatically computing or pointing-and-clicking and dragging-and-dropping by means of a computer, at least one combination of a sample and a stain set defined in (a) and (b); (d) automatically computing, or pointing-and-clicking and dragging-and-dropping by means of a computer, to create a list controls necessary to interpret data obtained from the experiment, the list to include (i) single-stain controls necessary to apply fluorescence compensation to the data obtained from the experiment, (ii) unstained controls necessary to determine autofluorescence levels for cell samples, and (iii) FMO controls necessary to identify the boundary between unstained and dully stained cells for a given marker with a given stain set; (e) computing the volumes and diluents necessary to prepare stock solutions and cell suspensions in sufficient amounts at appropriate dilutions for pipetting into the tubes or wells of an experiment, (f) generating an editable pipetting plan that combines stain sets and controls with samples and locates these in an array suitable for use as a guide for automatic or manual pipetting of the experiment, (g) enabling either automatic or user selected printing of experiment execution information containing at least one of (i) the (edited) pipetting plan with the location of the samples, stain sets and controls in the array; (ii) the amounts of the (diluted) samples, stain sets and controls to be added to the locations in the array; (iii) the total volumes of individual reagents, stain sets, samples, and diluents required for the experiment, (iv) the available amounts of each reagent; (v) the storage location of the reagents; (vi) the designated measurement instrument for the experiment; and (vii) the properties of the measurement instrument; (h) generating an XML or other standards-defined machine readable file containing at least one of the items in (g i-vii), and (i) enabling controlled internet access to the file created in (h).

According to some embodiments, the generating of the experiment plan further comprises: (i) determining a dilution of the reagent combination, (ii) calculating a volume of the reagent combination, (iii) calculating a volume of a sample population of cells, and (iv) determining a quantity of at least one fluorescent dye for use in creating a multiparameter Hi-D stain set for flow cytometry or fluorescence microscopy.

According to some embodiments, the generated experiment plan is maintained in digital form in a computer. In some embodiments, it is password protected to restrict its use to specified users. In some embodiments, the experiment plan can be copied in editable form and can be edited for reuse. In some embodiments, data generated pursuant to the experiment plan can be manually or automatically linked via hyperlinks, shortcuts, an association between the files, and other similar means of connecting information and documents. In some embodiments, the experiment plan can be stored in the same directory/folder/location on the computer.

According to some such embodiments, the generated experiment plan can be served by a computer. According to some implementation, the client software can transmit automatic or user requests to the server to transfer of the experiment plan to a computer on which the data will be collected. According to some embodiments, the client operates on the data collection computer to interpret the experiment plan and to transfer elements of it to the data collection software with which the data will be collected. According to some embodiments, the data collection computer runs data collection software such as the DiVa (BD Biosciences, San Jose, Calif.) data collection software, which can display sample identifications, keywords, reagent labels, and reagent-fluorochrome combinations during data collection. According to some embodiments, the data collection software can enable users collecting data to use the transferred experiment plan information to guide data collection with the data collection software. The data collection software also can use the transferred information to label the data and data files generated during data collection.

According to some embodiments, the client may directly add experiment protocol information to data files after each file is collected or after all data files have been collected. According to some embodiments, the client may (1) run on the computer on which the data are collected, or (2) run on a different computer. According to some embodiments, the client may call for automated compensation for a set of data files once data collection has terminated. According to some embodiments, the automated compensation process may use experiment protocol information in the generated file that was transferred from the protocol design computer to the client running on the data collection computer. According to some embodiments, the client provide an interface through which users can (a) accept client-defined provisional associations between experiment protocol information and samples that have been collected with incomplete experiment protocol information, or (b) make corrections in these assignments.

According to some such embodiments, the client automatically packages the data files for the experiment together with the experiment protocol information file and adds a "check sum" or other manifest inspection tool that henceforth allows detection of data loss or modification from the package. According to some embodiments, the client software running on the data collection instrument may transfer the set of data files collected for an experiment to a well-managed online archive. According to some such embodiments, the archive can automatically catalog the data files. The archive also can include a server computer to allow a user to access the data files via a computer network. According to some embodiments, the archive can be running data EverTrieve archiving software at woodsidelogic.com. According to some embodiments, client maintains a copy on the computer on which the client is operating until the archive signals that the copy may be destroyed. According to some embodiments, this signal is dependent on the archive having written at least one copy of the data to an online data storage location and at least one additional copy to a safe archive location. According to another embodiment, this safe location is archival storage media such as, but not limited to, a DVD or BluRay disk. According to some such embodiments, the archive automatically catalogs the data files according to the experiment protocol information in the file that was transferred initially to the client.

According to some embodiments, the archive can track the online and offline location(s) of the transferred data files along with the protocol information for the files and the overall experiment. According to some embodiments, the archive also can include a server computer to allow a user to access the data files via a computer network. According to some embodiments, the archive server provides the users with URI that it translates internally to URL to allow users to directly retrieve their data.

According to some embodiments, the archive server offers a controlled user interface to its catalog and displays the catalog data to allow users to find and retrieve their data. According to some embodiments, that archive catalog displays experiment information for at least one data set stored in the archive. According to some embodiments, the experiment information that is display may include sample descriptions or may list the reagents and fluorochromes in the stain sets experiment.

According to some embodiments, the archive may serve one or more stored data sets to one or more analysis packages in response to a user request or command. According to some embodiments, the archive may automatically serve stored data sets to analysis packages and triggers analyses.

According to another embodiment, the method further comprises generating analysis output based on (i) the generated experiment data and (ii) the generated experiment plan. According to some embodiments the archive or the software running on the data collection computer performs data processing steps on collected data. According to some embodiments, the data processing may include automatic application of fluorescence compensation to the data. According to some embodiments, the data processing may include user-requested application of fluorescence compensation to the data. According to some embodiments, the archive or the client software running on the data collection computer may add instrument descriptions or other information to the data files.

According to another embodiment, the method further comprises generating at least one hyperlink to the data files on the archive to access the data files via a computer network, and storing at least one hyperlink on the computer. At least one hyperlink can be automatically linked, i.e., automatically can refer, to the generated experiment data and the generated experiment plan, and at least one hyperlink can be stored in the same directory/folder/location as the analysis results.

According to another embodiment, the analysis output, or a hyperlink to the analysis output, can be stored in the same computer directory/folder/location as the generated experiment plan.

According to some embodiments, a location can be prepared on a computer to enable the hyperlink to be stored in association with the generated protocol design for the experiment. According to some embodiments, the hyperlink can be stored in a directory/folder/location associated with the protocol design information. According to some embodiments, the hyperlink can be used to maintain the results of data analyses for the experiment in association with the protocol design. According to some such embodiments, this directory/folder/location can be assigned by the protocol design software and can exist on the computer on which the protocol design software operates.

According to another aspect, the described invention provides a system 100 to streamline the locating, ordering, and re-ordering of at least one reagent from at least one supplier 140 for use in an experiment when an available amount on hand is insufficient for the experiment. The system 100 includes a computer 110 and a personal reagent shopper 130 (see FIGS. 7A and 7B). The computer may be connected to a data repository 120 and a second data repository 150 via a computer network. Reagent information may be received from the data repository 120 according to cell surface marker information that is transmitted from the computer 110 to the data repository 120. The personal reagent shopper 130 may be usable by the computer 110 to search the second data repository 150 for at least one reagent according to the reagent information received from the data repository 120. The second data repository 150 may contain an inventory of reagent combinations or ingredients for the in reagent combinations. The second data repository may be connected to at least one supplier 140 via a computer network to provide an updated inventory of reagent combinations and ingredients as well as to provide a user with access to order the reagent combinations and ingredients from at least one supplier 140. The personal reagent shopper 130 may automatically or manually order a quantity of at least one reagent from at least one supplier 140 when the available amount on hand is insufficient for the experiment. The personal reagent shopper 130 may be a software based program. The personal reagent shopper 130 may be located on the computer 110 or may be accessible on the computer 110 via a computer network. The personal reagent shopper 130 may order the reagent from the supplier 140 via a computer network.

According to one embodiment, the personal reagent shopper 130 may automatically or manually order, or cause to be ordered, a second quantity of at least one reagent from a secondary supplier when an amount available from a first supplier is insufficient for the experiment. According to some such embodiments, the personal reagent shopper 130 may determine that a reagent, reagent combination, or ingredient for use therein that is available from a first supplier is insufficient for the experiment. In such a scenario, the personal reagent shopper may order, or cause to be ordered, a first quantity from the first supplier and a second quantity from the second supplier in order to obtain an amount needed to conduct the experiment.

Several non-limiting examples of a computer 110 are a personal computer (e.g., desktop computers or laptop computers), personal digital assistants (PDAs), wireless devices, cellular telephones, internet appliances, media players, home theater systems, media centers, and the like. For the purposes of this disclosure, a computing device includes a processor and memory for storing and executing program code, data and software, and may be provided with an operating system that allows the execution of software applications in order to manipulate data. The computer 110 can include one or more input devices, e.g., keyboard, keypad, mouse, etc. and input device interface, for example: a display, such as a screen or monitor, which can be specified using any of a number of languages, including without limitation, a markup language such as Hypertext Markup Language, scripts, applets and the like.

Additionally, according to some embodiments, the system can generate a document in a standard electronic format, including, but not limited to XML (a markup language for documents containing structured information, which is an application profile of SGML, the Standard Generalized Markup Language defined by ISO 8879) via transfer of data to a data collection instrument. According to some embodiments, the data comprises a list of samples and their specifications. According to some embodiments, the data comprises a list of controls for compensation and Fluorescence Minus One (FMO) calculations. According to some embodiments, the data is transferred to the data instrument to be used for data collection and for automated compensation, i.e., once the data is entered, compensation and relevant computations may be applied. According to one embodiment, the data is transferred to the data instrument automatically. According to one embodiment, the data is transferred to the data instrument manually. According to some embodiments, the system generates a report that imports information needed for automated computation/application of the compensation algorithms and the FMO algorithms. According to some embodiments, the system generates a report which is transferred to the data collection instrument directly by the data collection instrument. According to some embodiments, the system generates the report independent of the data collection instrument For the purposes of this disclosure a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

According to another embodiment, the method further comprises automatically estimating fluorescence compensation.

According to another embodiment, the method further comprises automatically estimating fluorescence compensation based on the fluorescence properties of the combination of fluorescent reagents specified by any of the methods for specifying the markers and reagents in stain sets specified above.

In some such embodiments, the system will identify the data sets for which fluorescence compensation is required and reveal the specific stain set reagent specifications required for implementing said compensation for each data set. In another embodiment, the system will directly transfer said information to the utility employing the method for estimating fluorescence compensation. In another embodiment, the system will trigger the fluorescence compensation automatically by transferring said information to the compensation utility. In some implementations, the system will transfer said information in association with the data sets or will cause the said information to be so transferred. In some implementations, the system will write said information directly into the data sets in a form that will allow it to be used to implement fluorescence compensation algorithms.

2. Method for Estimating Fluorescence Compensation

The described invention further provides a model-based approach for evaluating a coefficient matrix for estimating fluorescence compensation from raw fluorescence measurements in multi-color flow cytometry.

The described model is based on the physics of fluorescence and light detection using photomultipliers (PMT) and accounts for background light (when no cells are present), autofluorescence (from cells with no specific stain) and specific fluorescence signals from an arbitrary number of fluorochromes as long as the spectra can be resolved with appropriate detectors (meaning that generally that there is one detector "tuned" to efficiently detect each of the fluorochromes). This model-based approach allows for computation of statistically valid "quality-of-fit" measures, which are critically important for quality assurance and which make it feasible for the method to be applied in an unsupervised or fully automatic manner.

The described model takes into account the pattern of expected variances as a function of signal level to improve the accuracy of the fit, replaces the reliance upon subjective gating to exclude the inappropriate events and to specify appropriate populations for evaluation of coefficient populations with an objective and automatic process, provides validation that is based on statistical quality of fit; provides estimates for coefficients useful in tracking the stability of reagents and instruments over times, and allows for the determination as to whether observed changes are significant or not. Human interaction only is necessary when the quality of fit falls outside of a statistically or historically defined range. The photoelectron scales that are estimated as part of the model provide information useful for other purposes; while photoelectron scales can be evaluated with special equipment or specific testing procedures, this information seldom is available on instruments used for biological work.

The described invention further provides for automated fluorescence compensation that does not rely on human-defined gating or reducing compensation control populations to their medians or similar measures, but rather uses all of the informative data points with their brightness distribution and measurement uncertainties to obtain optimal compensation and to extract confidence limits and other useful information. Therefore, unlike direct automation of existing methods, the described invention provides a reliable, non-supervised environment capable of detecting and reporting problems as they arise.

1.1. Poisson Statistics and Photoelectron Scaling

The described invention incorporates the use of the number of photoelectrons contributing to the fluorescence measurements. The photoelectron scaling for each fluorescence channel allows for the prediction of the distribution of measurements around the fit line in a single stained compensation control.

Finite photoelectron counts and Poisson statistics have an important role in setting limits on the ability to measure low level staining in fluorescence compensated samples.

Estimation theory concerns estimating the values of markers based on measured/empirical data. Estimation theory assumes that the desired information is embedded in a noisy signal. The purpose of estimation theory is to arrive at an estimator, which takes the measured data as input and produces an estimate of the markers. The markers describe an underlying physical setting in such a way that the value of the markers affects the distribution of the measured data. An estimator attempts to approximate the unknown parameters using the measurements.

For example, where an estimate of phycoerythrin, red [PE] in a FITC-positive cell population has a greater uncertainty than in a FITC-negative cell population, the FITC-positive cell population is more spread out in the PE dimension than the FITC-negative cell population and includes many cells whose estimated fluorescence is negative. This variation is an effect of the quantum nature of light, and of the limited amount of light generating the detected signal in each measurement channel. In this example, the detected signal is subject to what commonly are called "counting statistics" and thus is governed by the Poisson distribution. In practice, the limiting step is the number of photoelectrons emitted at the cathodes of the photomultiplier tubes (PMTs). The standard deviation of the actual measurements scales with the square root of the number of photoelectrons detected. Additional factors (for example, the number of photons emitted and the amplification factors at PMT dynodes) increase variation, making the estimates of photoelectron numbers from observed distributions slightly lower than the actual photoelectron numbers. This lower estimate is referred to as a "photoelectron estimate."

Calculations of spectral overlap used in carrying out fluorescence compensation should accurately represent the average behavior of the dyes in use, since they are based on control data from many cells. However, because the compensation correction is applied to data for individual cells, the statistical uncertainties in each measurement combine positively so that the uncertainty in measuring a particular dye amount in a multi-color stain will be greater than the uncertainty in measuring the same dye amount as a single stain. This may result in the subtractions being too low and the estimated values being too high for the actual amount of dye/signal associated with the cells. In some cases, the subtractions are too high and lead to estimates of the amount of dye/signal associated with individual cells that are negative (a physical impossibility). Collectively, however, the values for the over-estimated and under-estimated events combine into the correct value for the average dye content.

1.2. Construction of Model

When a cell or particle labeled by a single fluorochrome is measured in a flow cytometer, the signal detected in each fluorescence channel will come from several sources: (1) electronic noise, (2) background light not associated with the cell or particle, (3) fluorescence of the cell or particle not derived from the applied fluorochrome (autofluorescence), and (4) fluorescence from the applied fluorochrome. In well-designed systems using PMT detection, electronic noise should be negligible. In routine measurements, because its effects are not separable from those of background light, the background light element in the model incorporates any actual electronic noise effects. Each detector is designed to receive light excited by a particular laser and emitted in a particular wavelength region. In general, each detector channel is designed to optimally detect one fluorochrome, and its sensitivity to other fluorochromes used in a multicolor staining system will range from moderate to essentially zero. Thus, for each measurement event, the expected fluorochrome signal on each detector is proportional to the amount of dye times the efficiency factor of the detector for that dye. The total expected signal adds the background and autofluorescence to the amount of dye times the efficiency factor of the detector for that dye.

Since the measured signal in each detector is derived from a limited number of photoelectrons at the PMT cathode, measured signals include random variability related to "counting statistics" as specified by the Poisson distribution with a parameter related to the number of photoelectrons. It is the Poisson value, not the exact number of photoelectrons, that is relevant in modeling actual measurements. For the Poisson-related process of signal generation, the expected variance of measurements on a particular data channel at a particular dye level will be proportional to the total expected signal on that data channel. The standard deviation of measurements at a particular dye level is expected to increase with increasing dye level in proportion to the square root of the total signal, while the standard deviation relative to the mean is expected to decrease in proportion to the square root of the total signal.

The described inventive model addresses two practical problems in applying this model to data. First, the model accounts for the variance of the data points around the model predictions, which requires estimates of the background, autofluorescence distribution and photoelectron scaling. Second, the model accounts for the presence of outliers (such as, untypical cells, bits of fluorescent debris and a small percentage of cells or particles carried over from previous samples). These outliers tend to confound least squares fitting procedures. To avoid errors due to these sources of aberrant measurements, several preliminary robust (not sensitive to outliers) fitting steps are performed to estimate the error weights, the autofluorescence distribution, the autofluorescence background and the photoelectron scaling. The results of these preliminaries are used to prune the data to remove clear outlier events. Next the least squares method is used to fit each coefficient and estimate its accuracy. Finally, the full model is fit on the censored data to yield final estimates of the parameters and the overall quality of fit. At several points in the process, the results can be checked against statistical expectations and historical trends to ensure that the method is proceeding successfully.

According to one aspect, the described invention provides a method for estimating fluorescence compensation comprising the steps:

(1) Requiring as input (a) a sample of unstained cells or of reagent capture particles, and (b) a set of cell or particle samples labeled singly with each of the fluorochromes in use;

(2) Obtaining measurements of each of the samples in (1); and (3) Processing the resulting data set, wherein processing step (3) further comprises:

3.1) Estimating the mean and the standard deviation of the autofluorescence from the unstained sample for each detector (using robust methodology that is insensitive to outliers);

3.2) repeating following steps (3.3-3.14) for each single fluorochrome-labeled sample;

3.3) Excluding any event whose fluorescence is within 10% of the maximum observable signal on any detector. Typically there are nonlinearities in this region that can confound the method. In some embodiments, this step comprises excluding any events whose signal on the primary detector for the fluorochrome is less than two standard deviations above the autofluorescence mean. These events contribute very little information to the model;

3.4) Performing steps 3.5-3.10 for each of the other detectors;

3.5) Assuming initially that the background is zero and estimating the standard deviation of each event as being proportional to the square root of the absolute signal level on the primary detector for this fluorochrome;

3.6) Fitting a line through the mean of the autoflurorescence on this detector using a robust fitting procedure (such as, for example, minimum absolute scaled error) with errors scaled using the estimates computed in step 3.5;

3.7) Estimating the background signal level using the medians of the squared scaled errors of the brightest half of the fit data and the squared errors of the autofluorescence data around their mean;

3.8) Computing an improved estimate of the standard deviation of each event as the proportional to square root of the absolute signal level on the primary detector plus the estimated background;

3.9) Again Fitting a line and computing the scaled errors of fit for each point using the robust fit procedure and then compute the median squared scaled error of fit;

3.10) Estimating the photo electron sensitivity scaling using this median value and rescale all the errors so that the resulting errors should be chi squared distributed with one degree of freedom;

3.11) For each event totalling the square scaled error from all detectors, excluding outliers (for example, by rejecting any event with P<0.01 assuming a chi squared distribution with N−1 degrees of freedom; (N=number of fluorochromes));

3.12) For each detector performing the following steps 3.13-3.15;

3.13) Fitting a least squares line to the remaining data constrained to pass through the mean of the autofluorescence using the estimated standard deviations computed above. The slope of this line gives one coefficient in the effective spectrum matrix. This procedure also yields an estimate of the standard error of this coefficient;

3.14) Testing the assumption of linearity required by the model (for example, by applying the run test to the positive and negative errors to verify that they are randomly distributed);

3.15) Testing the standard error of the coefficient to ensure that the method is proceeding correctly; and 3.16) fitting the full model using a non-linear least squares procedure yielding final estimates of the background and the photoelectron scaling and an overall quality of fit value using the matrix of coefficients and all of the censored data set computed above; and testing the background and photoelectron scales against historical patterns to detect systematic problems with the instrumentation and to validate the quality of fit against its know distribution.

According to some embodiments, a photon estimate of the sensitivity of the detector results from the compensation calculation.

3. Method for Generating Multiparameter Experiment Data

According to another aspect, the described invention provides a method for generating multiparameter experiment data for the identification and quantification of at least one molecule in or on at least one cell with or without reference to at least one fluorescence property of at least one instrument-measurable atom or molecule associated with a reagent combination, the method comprising steps: (a) generating a plurality of reagent combinations comprising the plurality of reagents to detect a plurality of markers; and (b) generating a rank-ordered list of reagent combinations ranked according to at least one user-defined or system-defined criterion and determining an optimal reagent combination (rank order #1) based on at least one user-defined or system-defined criterion.

According to one embodiment, at least one of steps (a) and (b) is performed using a computer.

According to another embodiment, at least one of steps (a) and (b) is performed automatically.

According to another embodiment, step (a) further comprises the steps: (i) specifying, using a computer, a plurality of reagents that can detect or participate in the detection of on or more of the plurality of parameters; (ii) specifying, using a computer, at least one fluorescent dye or other instrument-measurable atom or molecule associated with each reagent; (iii) specifying, using a computer, a plurality of measurement instruments and the properties or measurement capabilities of each measurement instrument. According to some such embodiments, at least one of steps (i), (ii), and (iii) is performed by a computer. According to some such embodiments, at least one of steps (i), (ii), and (iii) is performed by a computer operating locally. According to some such embodiments, at least one of steps (i), (ii), and (iii) is performed by a remote computer.

According to another embodiment, step (b) further comprises the steps of (i) using a computer to acquire ranking criteria from the user, (ii) computing system-defined ranking criteria, and (iii) creating a rank-ordered list according to user-defined and/or system-defined criteria, (iv) displaying the rank-ordered list, and (v) enabling user and/or system-selection of reagent combinations based on placement on the rank-ordered list.

According to another embodiment, at least one user-defined or system-defined criterion is at least one of spectral interactions, detectors on an instrument, illumination sources on an instrument, amount of reagent on-hand, known reactivities of reagents in each reagent combination, known cross-reactivities of reagents in each reagent combination, properties of each reagent in each reagent combination, known sensitivities of reagents in each combination to treatments employed during the staining process, known sensitivities of reagent targets to treatments employed during the staining process, known or presumed amounts of reagent targets on particular cells or particles on which reagent targets are expressed, known reagent availability, availability of data acquisition and analysis capabilities, species of target cells, and species of reagent source.

According to another embodiment, the method further comprises steps: (i) generating an experiment plan based on at least one type of cell and the optimal reagent combination by using the computer to point-and-click or drag-and-drop subjects, samples, and keywords for the experiment; (ii) generating a ready-to-use pipetting plan based on the subjects, samples and keywords, and (iii) printing the ready-to-use pipetting plan.

According to some such embodiments, at least one of steps (i), (ii), and (iii) are performed by a computer.

According to some such embodiments, the generated experiment plan of step (i) is transferred to an instrument where the experiment plan is displayed via software on the instrument, and wherein the generated experiment data and the generated experiment plan are automatically linked and/or stored in the same directory.

According to some such embodiments, the generated experiment plan is transferable to a DiVa data collection software on the instrument. According to some such embodiments, the DiVa software displays sample names, keywords, reagent labels, and at least one fluorescent dye while the experiment data is being generated. According to some such embodiments, the DiVa software labels the generated experiment data. According to some such embodiments, the generated experiment data is stored in data files.

According to some embodiments, the data files are automatically transferable to a well-managed online archive. According to some such embodiments, the archive automatically catalogs the data files. According to some such embodiments, the archive includes a server computer to allow a user to access the data files via a computer network.

According to another embodiment, the method further comprises step: (i) generating analysis results based on the generated experiment data and the generated experiment plan. According to some such embodiments, the analysis results are stored in the same directory as the generated experiment data and the generated experiment plan.

According to some such embodiments, the method further comprises steps (i) generating at least one hyperlink to the data files on the archive to access the data files via a computer network; and (ii) storing the at least one hyperlink on the computer. According to some such embodiments, the at least one hyperlink is automatically linked to the generated experiment data and the generated experiment plan. According to some such embodiments, the at least one hyperlink is stored in the same directory as the analysis results.

4. System for Ordering and Managing Reagents

According to another aspect, the described invention provides a system to streamline the availability (e.g. locating, ordering, and re-ordering) of at least one reagent from at least one supplier for use in an experiment when an available amount on hand is insufficient for the experiment, the system comprising components: (a) a computer connected to a data repository via a computer network; and (b) a personal reagent shopper usable by the computer to search the data repository for at least one reagent, wherein the personal reagent shopper orders a quantity of at least one reagent from at least one supplier when the available amount on hand is insufficient for the experiment. According to some embodiments, the system takes into account a plurality of factors, including, but not limited to, (i) the company from which a reagent is bought; (ii) cost of the reagent if comparison shopping is required; (iii) the amount of the reagent on hand; (iv) the amount of reagent present but spoken for; and (v) the plurality of companies from which the reagent can be obtained, such that the universe of available reagents is defined and the user can choose from any combination of vendors within that universe.

According to some embodiments, the system provides a "lab reagent catalog" in which a researcher can view reagents and related products currently in the possession of, or accessible to, people working in the researcher's laboratory or work group. According to some embodiments, this catalog facilitates efficient stain set design, deployment and optimization by making the possession and location of useful reagents transparent to researchers needing access to such. According to some embodiments, the catalog makes it possible for a researcher to reserve reagents for an experiment sometime before the experiment will be executed but to release the reserved reagents if they are not needed or if a greater need for the reagents develops elsewhere in the laboratory.

According to some such embodiments, the lab catalog comprises a user-interface (UI). According to some such embodiments, the lab catalog UI provides for at least one check box. Such check boxes include, but are not limited to, those that display (i) private reagents, (ii) public (to the current lab) reagents, and (iii) everyone's private reagents. Optionally, access to the display of each check box may be limited to certain users. According to some such embodiments, the lab catalog UI provides for at least one column. Such columns include, but are not limited to, a "Review" column (allows for review of the local (KB) version of reagents with the downloaded version, and a "Private" column (allows for a switch or toggle of the reagent between private reagents and public reagents. According to some such embodiments, the lab catalog UI optionally provides for at least one operation button. Such operation buttons optionally may be enabled constantly, upon login, or upon exit.

According to some such embodiments, the lab catalog UI provides for a plurality of preferences. Such preferences include, but are not limited to, private settings and synchronization. According to some such embodiments, "private settings" is used to set the default value of "private" column for a new/imported reagent. This preference tells the system where to keep/place the new/imported reagent, either "mine" (true) or under "my lab" (false).

According to some such embodiments, "synchronization" is used to enable either "automatic synchronization" (update catalogs without notifying the user) or "manual (notification and user acceptance)" when catalogs updates are available.

According to some such embodiments, the lab catalog UI provides for a plurality of filter check boxes or other controls that provide similar capabilities. According to some such embodiments, the filter check boxes allow the user to control what is displayed by the UI.

According to one embodiment, the component (b) the personal reagent shopper can be instructed by the lab catalog to automatically order a quantity of at least one reagent when supplies of one or more reagents dip below individually preset inventory levels.

According to another embodiment, the personal reagent shopper can order a second quantity of at least one reagent from a secondary supplier when an amount available from at least one supplier is insufficient to restore inventory levels or to supply at least one reagent for a specified experiment.

5. Method for Determining the Effective Spectrum Matrix

According to another aspect, the described invention provides a method for determining the effective spectrum matrix used in a flow cytometer, the method comprising steps: (a) measuring the autofluorescence of a set of unstained cells or reagent capture particles with each detector of a flow cytometer, wherein autofluorescence data is obtained from each detector; and wherein the mean and standard deviation of the autofluorescence data measured by each detector is determined; (b) measuring the fluorescence of a set of cells or particle samples labeled singly with each fluorochrome of a plurality of fluorochromes, wherein each fluorochrome of the plurality of fluorochromes is assigned a primary detector of a flow cytometer, wherein fluorescence data is obtained from each assigned primary detector of each fluorochrome of the plurality of fluorochromes; (c) analyzing the fluorescence data from each assigned primary detector of each fluorochrome of the plurality of fluorochromes of step (b), the analysis comprising: (i) excluding any measurement of fluorescence wherein the fluorescence is within 10% of the maximum observable signal on any detector of the flow cytometer; (ii) excluding any measurement of fluorescence recorded on the primary detector for the fluorochrome where the fluorescence recorded is less than two standard deviations above the mean of the autofluorescence data of step (a); thereby determining the effective spectrum matrix used in flow cytometry for fluorescence compensation.

According to one embodiment, the method further comprises the steps: (d) analyzing the fluorescence data from each assigned primary detector of each fluorochrome of the plurality of fluorochromes of step (c), the analysis comprising steps: (i) assigning the background value for each assigned primary detector of each fluorochrome of the plurality of fluorochromes to a value of 0, wherein the standard deviation of each fluorescence measurement from each assigned primary detector of each fluorochrome is estimated as being proportional to the square root of the absolute signal level on the primary detector of the fluorochrome; (ii) using a robust fitting procedure to fit a line through the mean of the autofluorescence data of each detector, wherein errors are scaled using the estimates computed in step (i); (iii) estimating the background signal level by using the medians of the squared scaled errors of the brightest half of the fit data and the squared errors of the autofluorescence data around their mean; (iv) computing an improved estimate of the standard deviation of each event as the proportional to square root of the absolute signal level on the primary detector plus the estimated background; (v) computing the median squared scaled error of fit with a robust fitting procedure to fit a line wherein errors are scaled using each point; (vi) determining the photo electron sensitivity scaling using the median squared scaled error of fit of step (v), wherein all errors are rescaled so that the resulting errors are chi-squared distributed with one degree of freedom; and (vii) totaling the square scaled error from all detectors for each event, wherein outliers are excluded.

According to another embodiment, the method further comprises the steps: (e) fitting a least squares line to the remaining data constrained to pass through the mean of the autofluorescence using the computed estimated standard deviations, wherein the slope of the line provides one coefficient in the effective spectrum matrix.

Figure 7A:
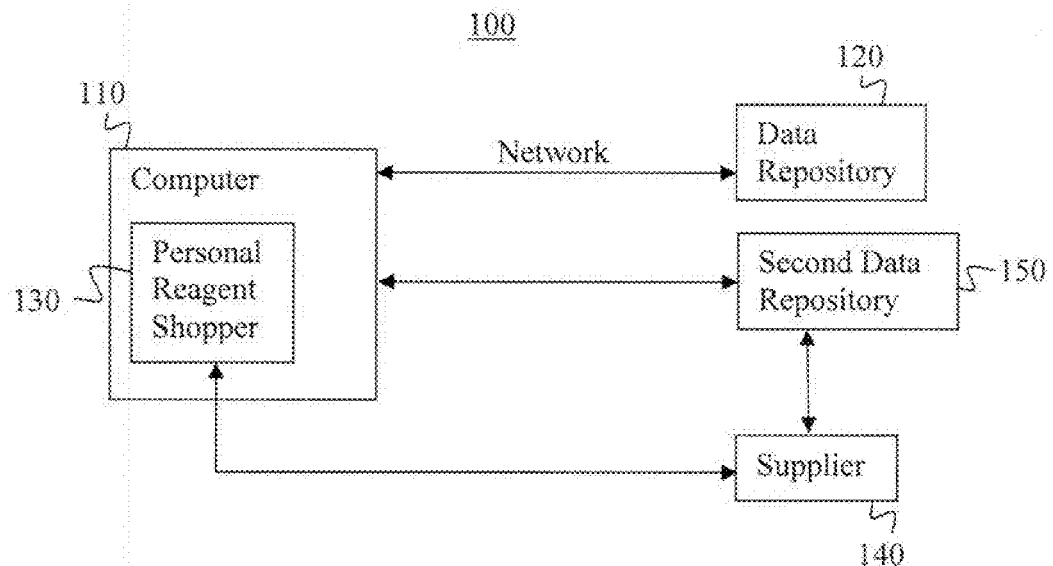
FIGS. 7A and 7B show block diagrams illustrating a system to streamline the locating, ordering, and re-ordering of at least one reagent.
Figure 7B:
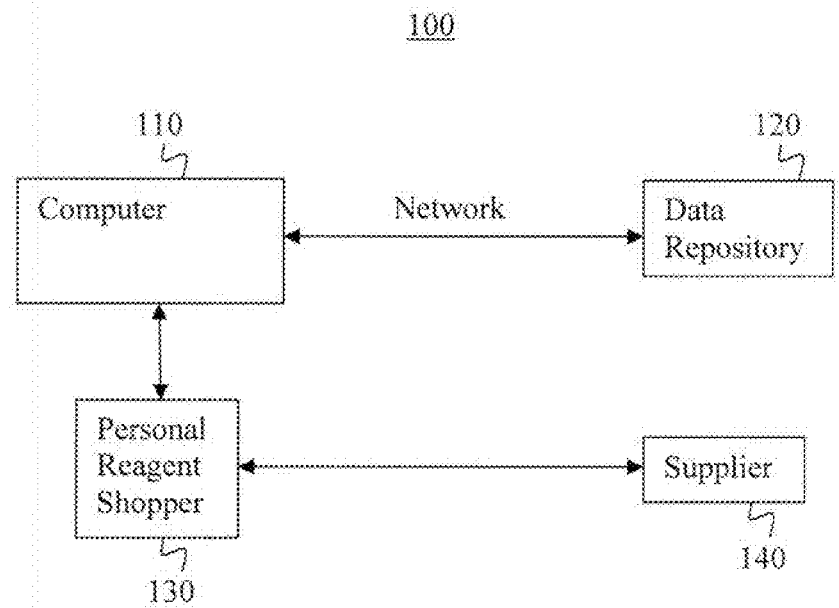
Figure 18:
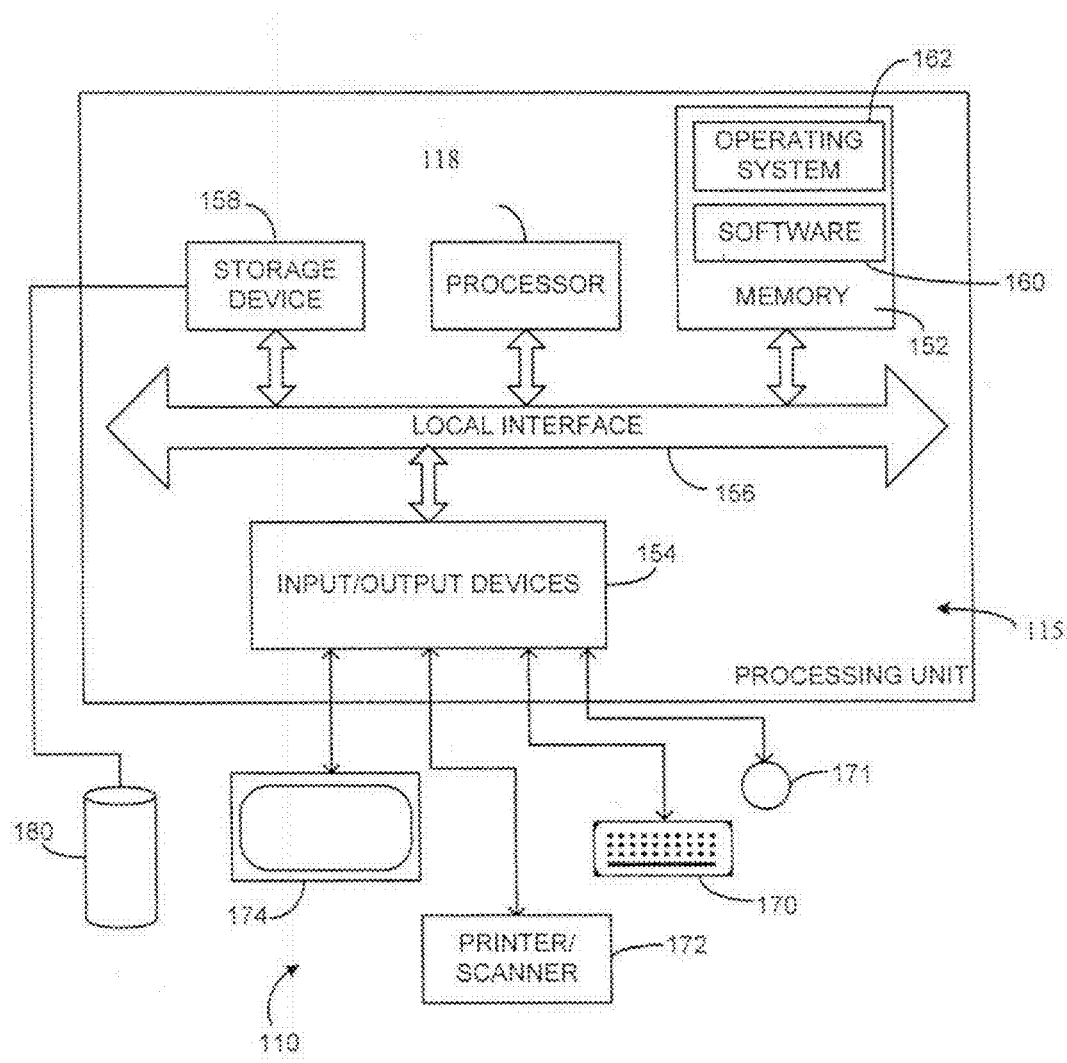
FIG. 18 shows an illustrative diagram of an embodiment of the hardware architecture where a computing device, as part of a multiparameter reagent combination selector and automated fluorescence compensator system, is communicatively coupled via a local interface.

Generally, in terms of hardware architecture, for example, as shown in FIG. 18, a computing device, such as computer 110, shown in FIGS. 7A and 7B as a part of a multiparameter reagent combination selector and automated fluorescence compensator ("selector/compensator") system 100, according to aspects of an embodiment of the claimed subject matter, can be a "computing device," which, by way of example may comprise a computer processor unit 115 which can include a processor 118, a memory 152, and one or more input and/or output (I/O) devices 154 (or other peripherals) that may be communicatively coupled via a local interface 156. The local interface 156 may be, for example, but not limited to, one or more buses or other wired or wireless connections. The local interface 156 may have additional elements, which are omitted for simplicity, such as controllers, buffers (caches), drivers, repeaters, and receivers, to enable communications, e.g. to data repositories 120 or 150 or supplier 140 as illustrated in FIGS. 7A and 7B. Further, the local interface 156 may include address, control, and/or data connections to enable appropriate communications among the aforementioned components.

The processor unit 115 may be a hardware device for executing software, e.g., that stored in memory 152. The processor 118 may be any custom made or commercially available processor, a central processing unit (CPU), an auxiliary processor among several processors associated with the processing unit 115, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc, or a 68xxx series microprocessor from Motorola Corporation. The processing unit may comprise a controller, microcontroller, or a hard wired, including firmware, device, or any combination thereof, or any other processor capable of performing logic driven operations, under partly or fully programmable instructions.

The memory 152 can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 152 may incorporate electronic, magnetic, optical, and/or other types of storage media. Note that the memory 152 can have a distributed architecture, where various components are situated remote from one another, but can be accessed by the processor unit 115, including as an example storage 158 and database(s) 180.

The software 160 in memory 152 may include one or more separate programs, each of which comprises an ordered listing of executable instructions for implementing logical functions. In the example of FIG. 18, the software 160 in the memory 152 may include the selector/compensator system software or parts of either, such as the personal reagent shopper 130 shown in FIGS. 7A and 7B, in accordance with the disclosed subject matter as discussed above, and a suitable operating system (O/S) 162. A non-exhaustive list of examples of suitable commercially available operating systems 162 is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time Vxworks operating system from WindRiver Systems, Inc.; or (g) an appliance-based operating system, such as that implemented in handheld computers or personal data assistants (PDAs) (e.g., PalmOS available from Palm Computing, Inc., and Windows CE available from Microsoft Corporation); or any other suitable operating system, including a customized operating such as may come installed on a diagnostic device or instrument, such as medical diagnostic or instruments, including a cytometer. The operating system 162 essentially controls the execution of other computer programs, such as the selector/compensator system computing device 110, illustrated by way of example in FIG. 18 and provides scheduling, input-output control, file and data management, memory management, and communication control and related services.

The selector/compensator system computing device 110 may be a non-transitory source program, executable program (object code), script, or any other entity comprising a set of instructions to be performed. When a source program, then the program needs to be translated via a compiler, assembler, interpreter, or the like, which may or may not be included within the memory 152, so as to operate properly in connection with the O/S 162. Furthermore, the selector/compensator system computing device 110 or individual portions thereof may be written as (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada or standard Internet languages, such as XML or HTML.

The I/O devices 154 may include input devices, for example but not limited to, a keyboard 170, mouse 171, printer/scanner 172, microphone (not shown), touch screen 174, etc. Furthermore, the I/O devices 154 may also include output devices, for example but not limited to, a printer/scanner 172, display 174, etc. Finally, the I/O devices 154 may further include devices that communicate both inputs and outputs, for instance but not limited to, a modulator/demodulator (modem; for accessing another device, system, or network) (not shown), a radio frequency (RF) or other transceiver (not shown), a telephonic interface (not shown), a bridge (not shown), a router (not shown), etc. Any of the foregoing may serve to connect the computing device processing device 115 with other computing devices, sources of input/recipients of output, such as a cytometry diagnostic apparatus.

If the computing device processing unit 115 is a PC, workstation, or the like, the software 160 in the memory 152 may further include a basic input output system (BIOS) (omitted for simplicity). The BIOS is a set of essential software routines that initialize and test hardware at startup, start the O/S 162, and support the transfer of data among the hardware devices. The BIOS may be stored in ROM so that the BIOS can be executed when the computing device processing unit 115 is activated.

When the computing device processing unit 115 is in operation, the processor 118 may be configured to execute software 160 stored within the memory 152, to communicate data to and from the memory 152, and to generally control operations of the computing device processing unit 115 pursuant to the software. The selector/compensator system computing device 110 and the O/S 162, in whole or in part, but typically the latter, may be read by the processing unit 118, perhaps buffered within the processing unit 115, and then executed.

When the selector/compensator system computing device 110 is implemented in software, as is shown in FIG. 18, it should be noted that the selector/compensator system computing device 110 software can be stored on any computer readable medium for use by or in connection with any computing device related system or method. In the context of this disclosure, a computer readable medium may be any non-transitory electronic, magnetic, optical, or other physical device or means that can non-transitorily contain or store a computer program for use by or in connection with a computing device related system or method. The selector/compensator system computing device 110 software may be embodied in any computer-readable medium for use by or in connection with an instruction execution system, apparatus, or device, such as a computer-based system, processor-containing system, like the computing device processing unit 115, or other system that can fetch the instructions for the instruction execution system, apparatus, or device and execute the instructions. In the context of this disclosure, a "computer-readable medium" can be any non-transitory means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or non-transitory propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM), an electronically erasable programmable read only memory ("EEPROM"), a Flash memory (electronic), an optical fiber memory (optical), and a portable compact disc read-only memory (CDROM) (optical).

The present invention is described below with reference to block diagrams and/or operational illustrations of methods and devices to select a multi-parameter reagent combination and for automated fluorescence compensation. It is understood that each block of the block diagrams or step of the operational illustrations, and combinations of blocks in the block diagrams or steps in the operational illustrations, can be implemented by means of analog or digital hardware and computer program instructions.

These computer program instructions can be provided to a processor of a general purpose computer, special purpose computer, ASIC, or other programmable data processing apparatus (such as a "computing device," as further defined herein), such that the instructions, which execute, via the processor of the computing device, the functions/acts specified in the block diagrams or steps in the operational illustrations.

In some alternate implementations, the functions/acts noted in the blocks or steps can occur out of the order noted in the block diagrams or operational illustrations. For example, two blocks shown in succession can in fact be executed substantially concurrently or the blocks can sometimes be executed in the reverse order, depending upon the functionality/acts involved.

For the purposes of this disclosure the term "server" should be understood to refer to a service point which provides processing, database, and communication facilities. By way of example, and not limitation, the term "server" can refer to a single physical processor with associated communications and data storage and database facilities, or it can refer to a networked or clustered complex of processors and associated network and storage devices, as well as operating software and one or more database systems and applications software which support the services provided by the server.

For the purposes of this disclosure a computer readable medium stores computer data, which data can include computer program code that is executable by a computer, in a non-transitory machine readable form. By way of example, and not limitation, a computer readable medium may comprise non-transitory computer readable storage media, for tangible or fixed storage of data, or communication media enabling interpretation and storage of code-containing signals. Computer readable storage media, as used herein, refers to physical or tangible storage (as opposed to signals) and includes without limitation volatile and non-volatile, removable and non-removable media implemented in any method or technology for the non-transitory tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium. Modules may be integral to one or more servers, or be loaded and executed by one or more servers. One or more modules may grouped into an engine or an application.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client or server or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Unless defined otherwise, all technical terms used herein have the same meaning as commonly understood by one of ordinary skill in the art to which this invention belongs. Any methods and materials similar or equivalent to those described herein also can be used in the practice or testing of the present invention It must be noted that as used herein and in the appended claims, the singular forms "a", "and", and "the" include plural references unless the context clearly dictates otherwise.

EXAMPLES

The following examples are put forth so as to provide those of ordinary skill in the art with a complete disclosure and description of how to make and use the present invention, and are not intended to limit the scope of what the inventors regard as their invention nor are they intended to represent that the examples below are all or the only examples performed. Efforts have been made to ensure accuracy with respect to numbers used (e.g., amounts, temperature, etc.) but some experimental errors and deviations should be accounted for.

Example 1

Estimation of Fluorescence Compensation

For an initial fitting of the model to compensation control data, outliers were removed and a linear least squares criterion was applied to select the best fit spectral overlap value for each secondary measurement relative to each primary dye signal. The outliers removed were those with offscale measurements in any fluorescence channel, and events with fluorescence less than two standard deviations above the mean of unstained cells.

Table 1 shows that for a four-color set of compensation controls, the conventional hand gating for the compensation analysis in FlowJo and the model fitting method of the invention provided similar spectral overlap matrices, especially when considering that the least squares evaluation used in the fitting is likely to be affected by small numbers of events that are well outside the main population.

TABLE 1

|  | FlowJo Hand Gating | | | | Model Fitting | | | |
| --- | --- | --- | --- | --- | --- | --- | --- | --- |
| FL-A | (100%) | 11.7% | 2.32% | 0.30% | (100%) | 11.8% | 2.33% | 0.27% |
| PE-A | 2.27% | (100%) | 22.8% | 2.97% | 2.15% | (100%) | 23.0% | 2.83% |
| Cy5PE-A | 0.14% | 0.95% | (100%) | 22.5% | 0.09% | 0.88% | (100%) | 22.4% |
| Cy7PE-A | 0.25% | 1.99% | 0.88% | (100%) | 0.29% | 1.98% | 0.84% | (100%) |

The larger populations are entirely at low overlap levels with higher values in the model fit than in the FlowJo hand gating (as expected if the model fitting is being affected by data values that an experienced user would gate out as not part of the population).

Figure 8:
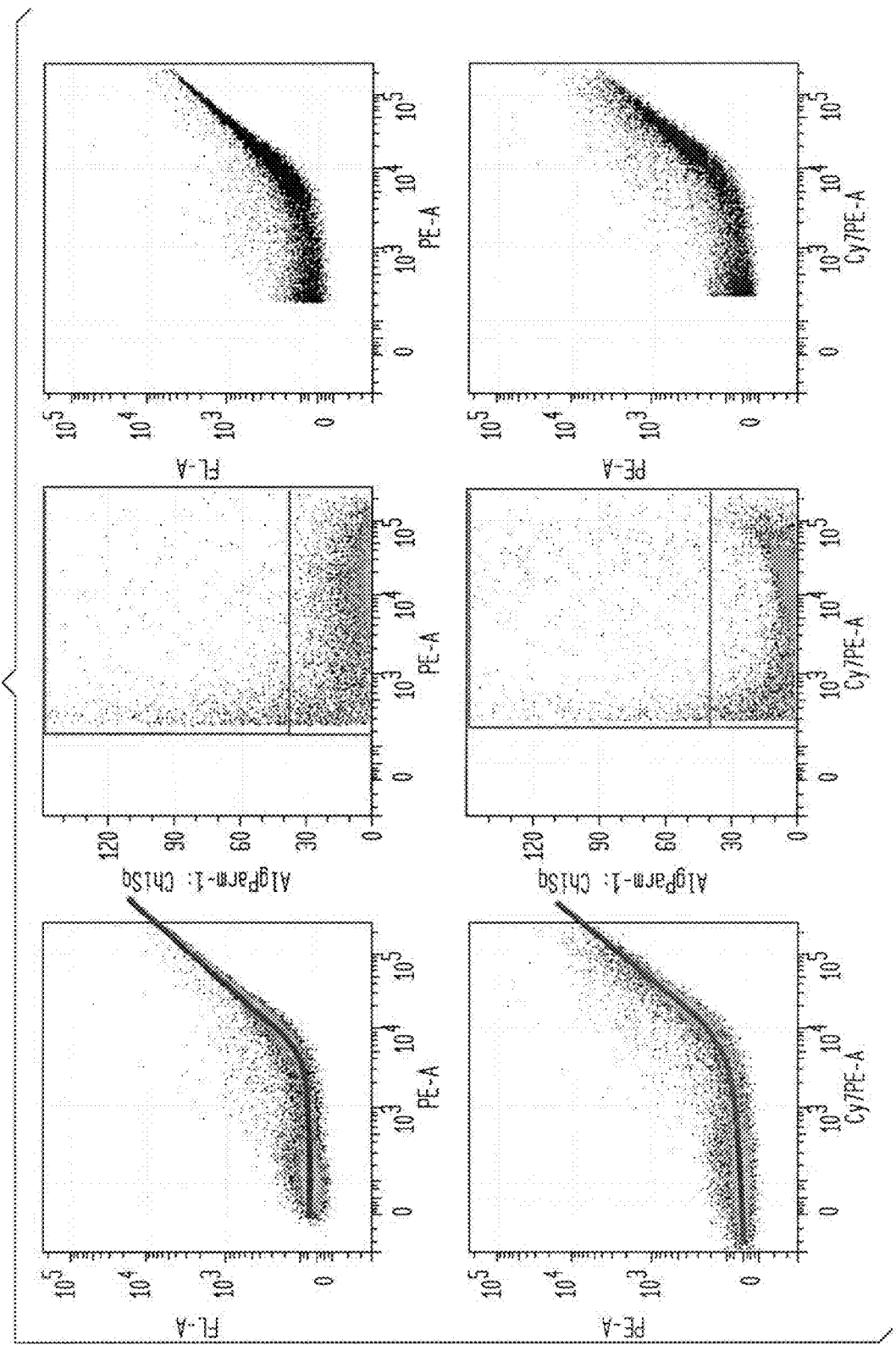
FIG. 8 shows an illustrative plots of single stain samples. The left panels show single stain samples with preliminary fit lines. ChiSq values (proportional to chi-square but not normalized) for each event in the cell population used in the fitting are shown in the middle panels in relation to the primary dye signal for the stain. The right panels show the fitted events classified as low (blue) or high (red) ChiSq by the gates drawn in the middle panels.

FIG. 8 shows that an objective and general criterion may be established to identify and exclude events that statistically are very unlikely to be part of the single stained population of interest in the fitting. The left panels show data from two single strains with the primary dye signal in the horizontal dimension and spectral overlap on another channel in the vertical. A line corresponding to the fitted spectral overlap is superimposed. The middle panels show the chi-square contribution for each data event in the fitted population (with outliers removed).

The ChiSq values are unnormalized but are proportional to actual chi-square values and are calculated from the deviations of the measured event from the fit line in each of the spectral overlap fluorescences. In each case, the main set of data points with low chi-square values (i.e., those close to the fit line) has ChiSq values below 40 and there are few data points with higher ChiSq values. Gating the data sets above and below 40 units (middle panel) leads to a new version of the left panel displays (low ChiSq data points (bright blue); the high ChiSq data points (bright red)). A new fit to the low ChiSq data should lead to an accurate and reliable spectral matrix for compensating data taken in concert with these controls.

The model provides additional information for analysis. For example, for the PE control in the upper middle panel, the ChiSq distribution appears to be uniform for all PE levels above $10^3$ (indicating correspondence with the model). In the lower middle panel, however, most of the data points around the $10^5$ signal level have systematically higher ChiSq values than those in the $10^3$ to $10^4$ range (indicating that the fit is not as good at the highest signal levels). In this example, the discrepancy may be due to the preliminary nature of the fit, and a revised fit is likely to show more uniformity in the ChiSq values. In a final fit, this kind of pattern may point to non-linearity in the measurements.

Example 2

Evaluating Photoelectron Scaling Using Single Stain Samples

The variation of data values around the fit line for a particular control sample viewed in the primary dye measurement dimension versus a spectral overlap dimension (see FIG. 8, left panels) derives from the Poisson distributed values in each data dimension based on the signal levels of the data events and the photoelectron scaling in each dimension. The effective variation in the secondary dimension is a composite of the Poisson scale effects in both measurement dimensions, and the details depend on the distribution of data events along the primary axis. Except in the case of measurements on particles with very uniform dye content, the separate photoelectron scales for the two measurement dimensions cannot be estimated separately using data from a single sample. However, in cases where two dyes have substantial spectral overlap each way (as illustrated in FIG. 8), an estimate of both photoelectron scales can be derived from the two data sets taken together.

Figure 9:
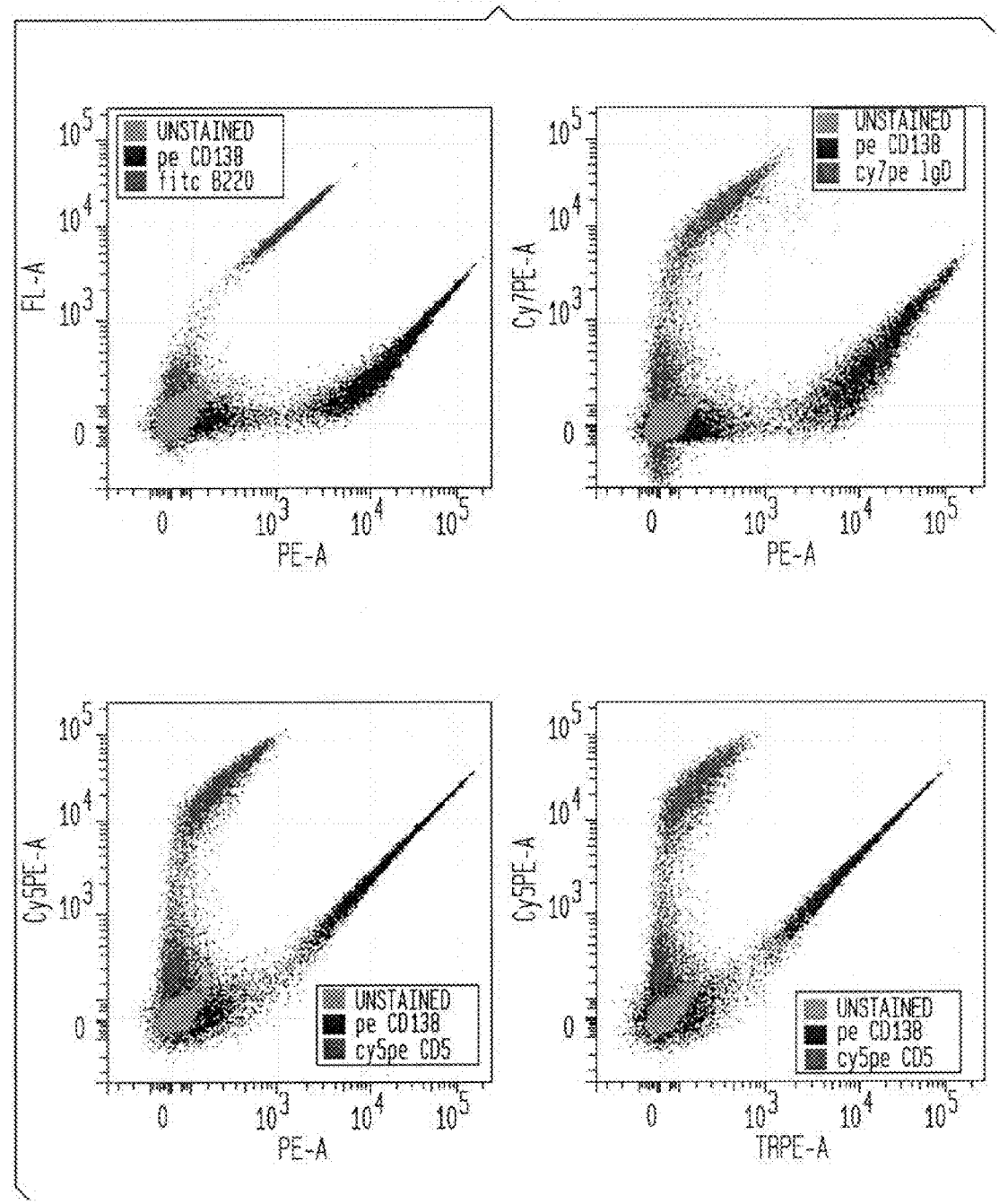
FIG. 9 shows illustrative plots of pairs of single samples showing spectral overlaps (uncompensated data). In each panel a phycoerythrin (PE) stain is shown in blue, and a single stain with the dye matching the vertical scale measurement is shown in red. An unstained cell population is shown in green.

FIG. 9 shows four examples of two single stain samples, each of which generates some signal on each of the selected detectors (with unstained cells overlaid in green). In each positive stain population (above approximately $10^3$ units), the relative width of the distribution of cell measurement events around the diagonal center line of the population is governed by the photoelectron values for the two detectors at points along the center line. This pattern corresponds to a defined statistical expectation, so that a particular "width" factor can be defined to characterize the pattern in each positive cell population.

The upper-left-to-lower-right positions of the center lines of the blue and the red positive populations correspond to different spectral overlaps. In the upper left panel of FIG. 9, for example, the blue PE pattern goes through approximately PE 40,000, FL 1000 which corresponds to a spectral overlap of 1000/40000=0.025 or 2.5%. The red population goes through roughly FL 9000, PE 1000 yielding spectral overlap 1000/9000=0.111 or 11%. Since the measurements are made with PMT detectors, we are justified in assuming that the observed "widths" derive from a process characterized by Poisson variation that scales with the numerical measurement scale in each dimension. The result is that the two photoelectron scale factors (for example, number of photoelectrons per 1000 scale units for each measurement dimension) can be derived from the two "width" factors and the two spectral overlaps measurable from pairs of data samples like those illustrated in FIG. 9.

When the photoelectron scale factor is known for a dye channel, scale factors can be evaluated even more simply for any channel onto which that dye has substantial overlap. In addition, as illustrated in the lower right panel of FIG. 9, a dye with overlaps onto two other channels (in this case PE) can provide one part of the data needed for a photoelectron scaling calculation (in this case between TRPE and Cy5PE). Therefore, it is expected that a set of compensation controls in almost any multi-color system will be usable for estimating photoelectron scaling on all of the measurement channel in use.

Since the photoelectron scale factor for a particular measurement channel at a fixed PMT voltage should be quite stable, it will not be necessary to evaluate it in every experiment. In addition, PMT gain vs. voltage characteristics are very well behaved and easy to evaluate, so photoelectron scale adjustments for differences in PMT voltage could be easily incorporated into the evaluation process.

Example 3

Reference Methods for Photoelectron Estimation

In typical flow cytometry, the accuracy of each fluorescence measurement fundamentally is limited by the uncertainty due to the finite number of photoelectrons generated at the PMT cathode. If a repeated measurement on highly uniform cells or particles resulted in a mean of N photoelectrons, it would be expected that the actual measurements follow a Poisson distribution for mean N in which the standard deviation equals the square root of N. In its simplest form, uniform light pulses with a suitable pulse shape, usually produced with a light-emitting diode (LED), are presented to a cytometer's fluorescence detectors, and the distribution of measured signals is analyzed. The coefficient-of-variation (CV) equal to (standard deviation)/(mean) often is used to characterize such distributions, and the photoelectron estimate is just $1/CV^2$. Thus, a distribution with a mean signal of 1000 units and a standard deviation of 100 units would have a CV of 0.1 or 10%, implying that the mean photoelectrons per measurement had been 100 ($=1/(0.1)^2$) or one photoelectron per 10 signal units.

High uniformity test particles are more readily available and easier to set up than an LED test system, and there is more assurance that the pulse shapes will match those of cells in regular measurements. However, the uniformity of signals from test particles will not be as good as the uniformity of LED pulses, so some estimate of the intrinsic distribution of the particles should be factored in. Finally, in real measurement systems, there is background light not associated with the particles of interest, which usually is subtracted out of the final measurement amplitude but which contributes to observed variation in low level measurements. Both a shaped pulse LED system and appropriate test particles may be used to measure the photoelectron scaling on all fluorescence channels of several cytometers.

Example 4

Validation of Photoelectron Scale Estimates Using Compensation Control Samples

The photoelectron scale estimates obtained with LED pulses and with high uniformity test particles will be compared with each other and with scale estimates derived from the new compensation control sample method. Measurements on at least several of the cytometers in the Stanford Shared FACS Facility will be included. The consistency of scales estimated from different compensation control data sets on each instrument will be analyzed and bias in the average of such estimations relative to the LED and test particle estimates will be analyzed. This investigation should lead to optimization of the methods used to characterize the dispersion around the fitted line of compensation control samples in order to obtain unbiased photoelectron scale estimates. It also should indicate how accurate the new method scales would be.

Example 5

Compensation Controls

Two kinds of data events that can bring confusion and distortion to analyses of compensation controls include (1) carryover from previous samples and (2) high autofluorescence more-or-less unstained cells within the sample. The automated analysis procedure will be tested with a series of samples in which increasing fractions of the data set consist of extraneous events.

To test for resistance to carryover, data files will be assembled from one compensation control plus various numbers of events from a different compensation control with substantial spectral overlap onto the primary dye channel of the initial sample. Unless the fit is constrained by knowledge of the approximate location of the population of interest, the method has to fail when a majority of the events are from the wrong sample. The automated analysis program will be analyzed to determine its capability to locate the proper population, exclude all of the contaminating events that are well above background in any measurement, and produce a spectral overlap matrix indistinguishable from what was found with no added contamination.

To test for effects of high autofluorescence cells, several compensation control sets will be selected in which the cell sample contains a substantial fraction of high autofluorescence cells, and the reagent staining is primarily on a low autofluorescence population. In this case, test data files will be constructed with a compensation control stain plus increasing additions of the unstained cell sample including high autofluorescence cells. In this case, some of the high autofluorescence events may appear close to the actual single stained population, presenting a challenge to the automated analysis program. The model will be analyzed to determine how much the spectral overlap matrix is affected by the contamination and to determine if there has been no significant shift in the matrix elements (unless the contamination is overwhelming and it becomes hard to identify the proper population).

Example 6

Automated Compensation Program

In order to exercise the new methods in a realistic research environment and provide a basis for efforts to make them generally available, a full function program that is sufficiently user-friendly, convenient and supportable to be used routinely in several FACS-based projects will be produced.

In this environment, software already is in place to provide the information required to launch the CompFree program. The FacsXpert system and/or the compensation control specification function in the BD Biosciences DiVa system already generate output files containing pointers to the FCS datafiles collected for each of the compensation controls and the reagent name and associated fluorochrome used in each control. Current FACS data management system, into which data is "checked in" once it is collected, uses this information to generate FlowJo launch files that include all the sample attributes and pointers to the actual data files for each experiment. Therefore, to acquire the information necessary to launch CompFree, a utility that will either use the FacsXpert or DiVa information directly, will be created or the compiled version in the FlowJo launch file will be used. With this information, a CompFree launch file will be created that will enable CompFree to identify automatically the controls, assign them to the appropriate dye channel, and locate and read in the data from the compensation control data files. No user intervention will be required.

Next, CompFree will evaluate the spectral overlaps and specify spectral overlap matrices that can be used individually to compensate all samples to which each set of compensation controls is relevant. The matrices then will either be written directly to the appropriate sample data files, so that they can be used with any FACS data analysis package capable of using such matrices, or appended to our current FlowJo launch file, along with instructions about which datafiles "belong" to each matrix. In either case, existing FlowJo routines will automatically compute the compensated data so that the compensated data is ready for the user to embark on analysis of the data in the experiment.

In addition to fully automating FACS data compensation, the CompFree version will report quality control evaluations derived from the fitting process, a reference copy of the normalized spectral overlap matrix and an estimate of the photoelectron scale in each fluorescence dimension derived from that experiment. Thus, it will provide "full service" automated compensation that will both decrease the time and effort required before the data can be analyzed and improve recognition of problems with the quality of the data before it is analyzed.

Example 7

Diagnostics

Maintaining optimal and matched laser alignments in multi-laser systems is important in that mis-alignments can produce data distortions, which degrade the accuracy of fluorescence compensated results even when they are not great enough to be seen as a problem in single channel measurements. If laser or detector alignments are not matched to each other, cells following different trajectories in the flow system will be evaluated with different relative efficiencies among the detectors. This means that the signal generated by a particular dye on its primary detector will not be as good a predictor as it should be of the spectral overlap of that dye's emission onto another detector. Equivalently, this means that fluorescence compensation cannot achieve its potential statistically limited accuracy. Detecting an alignment problem in an already collected data set may not allow for improvement of that data, but it will be a useful indicator that maintenance or service is needed.

If photoelectron scales have been established, misalignments will generate more variation of data values around the fit line than can be accounted for statistically. The excess variation will be evident particularly at high signal levels where the relative spread of the data around the fit line should be lowest (the left panels FIG. 8 show the expected pattern, which would be broadened if there were alignment problems). For mis-alignment between lasers, the discrepancy will be evident in data using dyes with primary detection on one laser but with substantial overlap on a channel derived from a different laser.

As a specific test of instrument alignment, this effect could be examined more sensitively by taking data sets with multi-dye test particles run at different flow rates. A specific data analysis routine for this kind of data could be produced readily based on some of the elements produced for compensation software.

Run tests may be used as a way to localize discrepancies between the fit line and the data. Results in which most data points in some signal level region fall above or below the fit line point to non-linearity somewhere in the measurement system. In this case, the events in the pruned data set used for fitting are ordered by their signal level in the primary dye channel and count "runs", sequences of successive events that are all above or all below the fit line. If there are data regions in which the events are biased significantly above or below, the runs analysis will show longer (and therefore fewer) runs than would be expected by chance, indicating probable non-linearity in the primary and/or secondary measurement.

Example 8

Lab Catalog

The user-interface (UI) of the lab catalog provides for easier sharing of reagents.

8.1. Reagent Book

FIG. 10 shows a screencap of a window of the user interface that includes check boxes, columns, and an operation button.

The lab catalog UI provides for a plurality of check boxes. Check boxes include, but are not limited to, those that display (i) private reagents ("mine"), (ii) public (to the current lab) reagents ("my lab"), and (iii) everyone's private reagents ("others"). Optionally, the access to the display of each check box may be limited to certain users (i.e., a "super user").

The lab catalog UI provides for a plurality of columns. Columns include, but are not limited to, a "Review" column and a "Private" column. The "review" column allows for review of the local (KB) version of reagents with the downloaded version. There will be a button in the column cell only when there is a conflict between the local and the server version of this reagent row (current row). The "private" column allows for a switch/toggle of the reagent between "Mine" and "My Lab." An operation/button ("get updates") is provided to get the latest lab catalogs updates from a server. This button will only be enabled when there is an update available. Optionally, the "get updates" button is available upon login or upon exit.

8.2. Preferences

Figure 11:
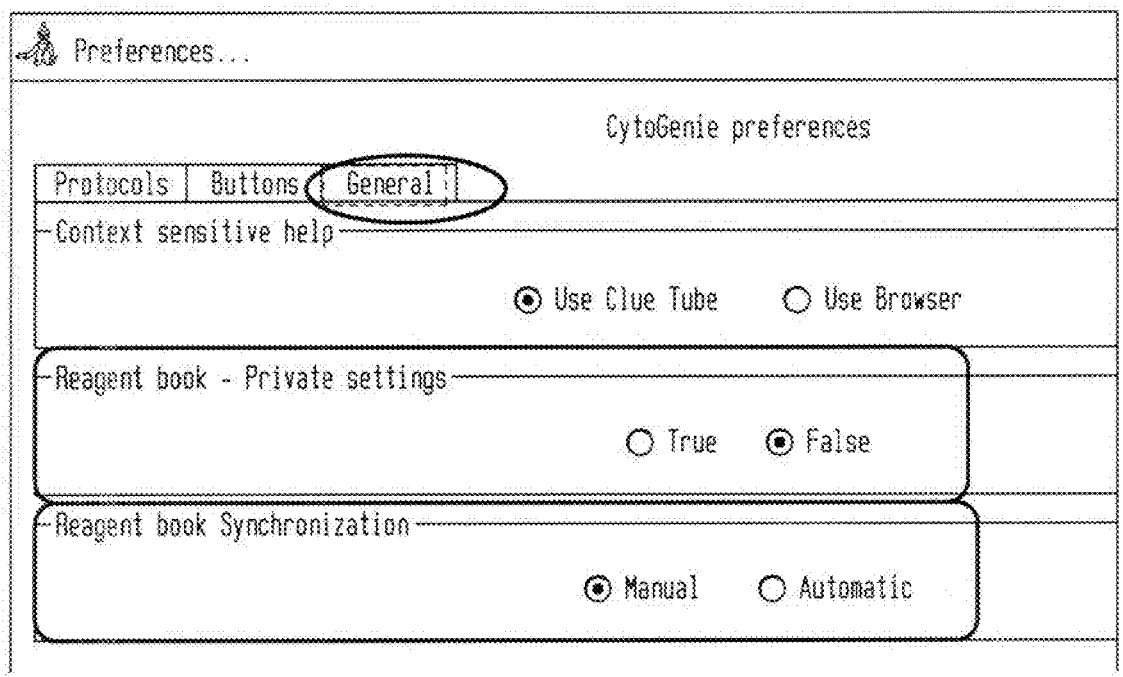
FIG. 11 shows a screencap of a window of the user interface where the user can select preferences.

FIG. 11 shows a screencap of a window of the user interface where the user can select preferences.

The lab catalog UI provides for a plurality of preferences including, but not limited to, private settings and synchronization. "Private settings" is used to set the default value of "private" column for a new/imported reagent. This preference tells the system where to keep/place the new/imported reagent, either "mine" (true) or under "my lab" (false).

"Synchronization" is used to enable either "automatic synchronization" (update catalogs without notifying the user) or "manual (notification and user acceptance)" when catalogs updates are available.

8.3. UI Controls: Functions

The lab catalog UI provides for a plurality of filter check boxes. These allow the user to control what is displayed by the UI. For example, a typical view after some reagents are imported by the user either by changing "Preferences private settings" before import as well as manually using the "private" column check boxes after import are shown in FIGS. 13-17.

FIG. 12 shows a screencap of an embodiment of a window of a filter check box where all check boxes are checked.

FIG. 13 shows a screencap of an embodiment of a window of a filter check box where only "mine" and "my lab" check boxes are checked.

FIG. 14 shows a screencap of an embodiment of a window of a filter check box where only "mine" is checked.

FIG. 15 shows a screencap of an embodiment of a window of a filter check box where only "my lab" is checked.

FIG. 16 shows a screencap of an embodiment of a window of a filter check box where only "generic" is checked.

FIG. 17 shows a screencap of an embodiment of a window of a filter check box where nothing is checked.

Example 9

Microscopy

Microscopy utilizes a stacked image of individual pixels in each color. In digital imaging, a pixel is a single point in a raster image, and is the smallest addressable screen element (i.e., it is the smallest unit of picture that can be controlled). Each pixel has its own address that corresponds to its coordinates. Pixels normally are arranged in a two-dimensional grid, and often are represented using dots or squares. In color image systems, a color is typically represented by three component (red, green, and blue) or four component (cyan, magenta, yellow, and black) intensities.

In some contexts, the term "pixel" is used to refer to a single scalar element of a multicomponent representation, while in others the term may refer to the entire set of such component intensities for a spatial position. In color systems that use chroma subsampling, the multi-component concept of a pixel can become difficult to apply, since the intensity measures for the different color components correspond to different spatial areas in such a representation.

Commonly, there are 4 stacked images (one for each color being detected) and 4 colors detected. Accordingly, the described invention, utilizing the algorithms described herein, provides for correction of fluorescence overlap in the stacked image on a pixel by pixel location basis.

While the described invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention. All such modifications are intended to be within the scope of the claims appended hereto.

What is claimed is:

1. A computer-readable storage medium tangibly storing thereon computer program instructions capable of being executed by a computer processor of a computing device, the computer program instructions defining steps for selecting and optimizing reagent combinations for identification or quantification of molecules in or on cells detectable by an instrument-measurable atom or molecule associated with the reagent combination, comprising:
   (a) specifying a plurality of markers to be detected by a plurality of reagents;
   (b) specifying at least one expected level of expression of one or more markers in a plurality of markers expected to be detected on or in each of a plurality of cells;
   (c) generating a plurality of reagent combinations comprising a plurality of reagents to detect the plurality of markers of step (a), wherein the reagent combinations are ranked according to at least one user-defined or system-defined criterion comprising efficacy of the reagent combination with regard to at least one type of cell;
   (d) optimizing the reagent combination by determining an effective spectrum matrix of an instrument comprising a plurality of detectors for estimating fluorescence compensation by
      (1) estimating background autofluorescence by measuring autofluorescence of a set of unstained cells or reagent capture particles with each of the plurality of detectors of the flow cytometer,
      (2) measuring fluorescence of a set of cells or particle samples labeled singly with each fluorochrome of a plurality of fluorochromes,
         wherein each fluorochrome of the plurality of fluorochromes is assigned a primary detector of a flow cytometer, and
         wherein fluorescence data is obtained from each assigned primary detector of each fluorochrome of the plurality of fluorochromes;
      (3) analyzing the fluorescence data from each assigned primary detector of each fluorochrome of the plurality of fluorochromes of step (b) by estimating the mean and standard deviation of the autofluorescence from the unstained sample in (a) for each detector; and
      (4) for each single fluorochrome labeled sample and each detector, estimating the standard deviation of each event by scaling errors with the estimates in (d), initially setting background to zero, and fitting a line through the mean of the autofluorescence data for each detector,
      (5) for each single fluorochrome labeled sample, estimating background signal level from the autofluorescence data; improving the estimate of the standard deviation of each event on the primary detector plus the estimated background; again fitting a line; and estimating the photoelectron sensitivity scaling by rescaling all errors to be chi squared distributed with one degree of freedom;
      (6) for each detector, fitting a least squares line to the remaining data constrained to pass through the mean of the autofluorescence, wherein the slope of the line provides one coefficient in the effective spectrum matrix; and generating final estimates of background, photoelectron scaling, and overall quality of fit by a nonlinear least squares procedure; and
   (e) providing a rank-ordered list of reagent combinations that fit within fluorescence spectral detection limitations of the instrument and within limitations imposed by treatment of the cells.

2. A method implemented by a computing device for selecting an optimal multimarker reagent combination for the identification and quantification of at least one molecule in or on at least one cell with or without reference to at least one property of at least one instrument-measurable atom, molecule, and molecular complex associated with the reagent combination, the method comprising:
   (a) specifying a plurality of markers to be detected by a plurality of reagents;
   (b) specifying at least one level of expression of one or more marker in the plurality of markers expected to be detected on or in each of a plurality of cells;
   (c) generating a plurality of reagent combinations each comprising the plurality of reagents to detect the plurality of markers in (a), wherein the reagent combinations are ranked according to at least one user-defined or system-defined criterion; and
   (d) estimating fluorescence compensation based on the fluorescence properties of the reagent combinations by determining an effective spectrum matrix of an instrument comprising a plurality of detectors for estimating fluorescence compensation by
      (1) estimating background autofluorescence by measuring autofluorescence of a set of unstained cells or reagent capture particles with each of the plurality of detectors of the flow cytometer,
      (2) measuring fluorescence of a set of cells or particle samples labeled singly with each fluorochrome of a plurality of fluorochromes,
         wherein each fluorochrome of the plurality of fluorochromes is assigned a primary detector of a flow cytometer, and
         wherein fluorescence data is obtained from each assigned primary detector of each fluorochrome of the plurality of fluorochromes;
      (3) analyzing the fluorescence data from each assigned primary detector of each fluorochrome of the plurality of fluorochromes of step (b) by estimating the mean and standard deviation of the autofluorescence from the unstained sample in (a) for each detector; and
      (4) for each single fluorochrome labeled sample and each detector, estimating the standard deviation of each event by scaling errors with the estimates in (d), initially setting background to zero, and fitting a line through the mean of the autofluorescence data for each detector,
      (5) for each single fluorochrome labeled sample, estimating background signal level from the autofluorescence data; improving the estimate of the standard deviation of each event on the primary detector plus the estimated background; again fitting a line; and estimating the photoelectron sensitivity scaling by rescaling all errors to be chi squared distributed with one degree of freedom;
      (6) for each detector, fitting a least squares line to the remaining data constrained to pass through the mean of the autofluorescence, wherein the slope of the line provides one coefficient in the effective spectrum matrix;

and generating final estimates of background, photoelectron scaling, and overall quality of fit by a nonlinear least squares procedure; and (e) providing a rank-ordered list of the reagent combinations that fit within fluorescence spectral detection limitations of the instrument and within limitations imposed by treatment of the cells.

3. The method according to claim 2, wherein at least one molecule is an activation marker, an antigen, a cell surface marker, a chromophore, a differential label, a dye, or a stain.

4. The method according to claim 3, wherein an expected level of expression of the at least one molecule on at least one cell type to be targeted by a stain set can be arbitrarily selected manually from a list of expression levels displayed by a computer.

5. The method according to claim 2, wherein the instrument-measurable atom, molecule or molecular complex is an antigen, an activation marker, a cell surface marker, a chromophore, a differential label, a dye or a stain.

6. The method according to claim 2, wherein step (a) further comprises the steps:
(i) specifying a plurality of reagents that can detect or participate in the detection of one or more of the plurality of markers;
(ii) specifying at least one fluorescent dye or other instrument-measurable atom or molecule associated with each reagent;
(iii) specifying a plurality of measurement instruments and the properties or measurement capabilities of each measurement instrument.

7. The method according to claim 6, wherein at least one of steps (i), (ii) and (iii) is performed by a computer.

8. The method according to claim 6, wherein step (i) the user interactively enters or chooses at least one marker to be detected by at least one stain set by entering at least one desired marker name or selecting at least one marker from a selection widget available on each row of a table-like structure in a column that displays markers already selected by at least one other method.

9. The method according to claim 2, wherein specifying step (a) is based on information from a genomic screen.

10. The method according to claim 2, wherein the at least one user-defined or system-defined criterion in (c) is at least one of spectral interactions, detectors on an instrument, illumination sources on an instrument, amount of reagent on-hand, known reactivities of reagents in each reagent combination, known cross-reactivities of reagents in each reagent combination, properties of each reagent in each reagent combination, known sensitivities of reagents in each combination to treatments employed during the staining process, known sensitivities of reagent targets to treatments employed during the staining process, known or presumed amounts of reagent targets on particular cells or particles on which reagent targets are expressed, known reagent availability, availability of data acquisition and analysis capabilities, species of target cells, and species of reagent source.

11. The method according to any one of claims 1 and 2, further comprising (f) selecting an optimal reagent combination.

12. The method according to claim 2, wherein the at least one property is fluorescence and fluorescence properties are selected from the group consisting of fluorochromes, lasers, filters, dye spectra, spectral overlap detection capabilities, and sensitivity of a fluorochrome to destruction by a treatment that occurs prior to, during, or after a given staining step.

13. The method of claim 2, wherein generating of the plurality of reagent combinations in step (c) further comprises the steps:
(i) transmitting cell surface marker information based on a surface marker characteristic of at least one type of cell to a data repository;
(ii) receiving reagent information from the data repository according to the transmitted cell surface marker information; and
(iii) generating the plurality of reagent combinations according to the reagent information from the data repository.

14. The method according to claim 2, wherein ranking step (d) is performed automatically according to a predetermined efficacy with regard to at least one type of cell.

15. The method according to claim 2, wherein ranking step (d) is performed manually according to user generated preferences.

16. The method according to claim 14, wherein the automatic ranking of the plurality of reagent combinations further comprises:
(i) determining whether an amount of each of the plurality of ingredients required for each of the plurality of reagent combinations is sufficient or insufficient;
(ii) excluding each of the plurality of reagent combinations for which the available quantity of any of the plurality of ingredients is insufficient; and
(iii) ranking the plurality of reagent combinations that have not been excluded.

17. The method according to claim 2, wherein the method is used for flow cytometry, and wherein the method further comprises identifying at least one type of cell by selecting at least one type of cell from the cells to react with at least one of the plurality of reagent combinations according to at least one surface marker characteristic of at least one type of cell.

18. A method implemented by a computing device for generating multimarker experiment data for identification and quantification of at least one molecule in or on at least one cell with or without reference to at least one fluorescence property of at least one instrument-measurable atom, molecule, or molecular complex associated with a reagent combination, the method comprising steps:
(a) specifying a plurality of markers that can be detected by a plurality of reagents;
(b) specifying a plurality of instrument-measurable molecules associated with the plurality of reagents;
(c) generating a plurality of reagent combinations each reagent combination comprising a plurality of reagents to detect a plurality of markers;
(d) specifying at least one level of expression of one or more marker in the plurality of markers of (c) expected to be detected on or in each cell in the plurality of cells
(e) optimizing the reagent combinations by determining an effective spectrum matrix of an instrument comprising a plurality of detectors for estimating fluorescence compensation by
(1) estimating background autofluorescence by measuring autofluorescence of a set of unstained cells or reagent capture particles with each of the plurality of detectors of the flow cytometer,
(2) measuring fluorescence of a set of cells or particle samples labeled singly with each fluorochrome of a plurality of fluorochromes,
wherein each fluorochrome of the plurality of fluorochromes is assigned a primary detector of a flow cytometer, and wherein fluorescence data is obtained from each assigned primary detector of each fluorochrome of the plurality of fluorochromes;

(3) analyzing the fluorescence data from each assigned primary detector of each fluorochrome of the plurality of fluorochromes of step (b) by estimating the mean and standard deviation of the autofluorescence from the unstained sample in (a) for each detector; and (4) for each single fluorochrome labeled sample and each detector, estimating the standard deviation of each event by scaling errors with the estimates in (d), initially setting background to zero, and fitting a line through the mean of the autofluorescence data for each detector, (5) for each single fluorochrome labeled sample, estimating background signal level from the autofluorescence data; improving the estimate of the standard deviation of each event on the primary detector plus the estimated background; again fitting a line; and estimating the photoelectron sensitivity scaling by rescaling all errors to be chi squared distributed with one degree of freedom;

(6) for each detector, fitting a least squares line to the remaining data constrained to pass through the mean of the autofluorescence, wherein the slope of the line provides one coefficient in the effective spectrum matrix; and generating final estimates of background, photoelectron scaling, and overall quality of fit by a nonlinear least squares procedure; and (f) generating a rank-ordered list of reagent combinations ranked according to fluorescence spectral detection limitations of the instrument and limitations imposed by treatment of the cells; and (g) selecting an optimal reagent combination.

19. The method according to claim 18, wherein at least one of the steps is performed automatically.

20. The method according to claim 18, wherein step (a) further comprises the steps:
(i) specifying a plurality of reagents that can detect or participate in the detection of one or more of the plurality of markers;
(ii) specifying at least one fluorescent dye or other instrument-measurable atom or molecule associated with each reagent;
(iii) specifying plurality of measurement instruments and the properties or measurement capabilities of each measurement instrument.

21. The method according to claim 18, wherein in (c), the reagent combinations are ranked according to at least one user-defined or system-defined criterion selected from the group consisting of spectral interactions, detectors on an instrument, illumination sources on an instrument, amount of reagent on-hand, known reactivities of reagents in each reagent combination; known cross-reactivities of reagents in each reagent combination, properties of each reagent in each reagent combination, available analysis capabilities, and species of an instrument.

22. The method according to claim 18, further comprising generating an annotated experiment plan based on at least one type of cell and the optimal reagent combination, the method comprising at least one of steps by using the computer for text entry,
(i) pointing-and-clicking or dragging-and-dropping subjects, samples, and keywords for the experiment;
(ii) generating a ready-to-use pipetting plan based on the subjects, samples, and keywords; and
(iii) printing the ready-to-use pipetting plan.

23. The method according to claim 22, wherein at least one of steps (i), (ii) and (iii) are performed by a computer.

24. The method according to claim 22, wherein the generated experiment plan of step (i) is transferred to an instrument where the experiment plan is displayed via software on the instrument, and wherein the generated experiment data and the generated experiment plan are automatically linked and/or stored in the same directory.

25. The method according to claim 24, wherein the generated experiment plan is transferable to a DiVa data collection software on the instrument;
wherein the DiVa software displays sample names, keywords, reagent labels, and at least one fluorescent dye while the experiment data is being generated;
wherein the DiVa software labels the generated experiment data; and
wherein the generated experiment data is stored in data files.

26. The method according to claim 25, wherein the data files are automatically transferable to a well-managed online archive;
wherein the archive automatically catalogs the data files; and
wherein the archive includes a server computer to allow a user to access the data files via a computer network.

27. The method according to claim 24, further comprising step:
(i) generating analysis results based on the generated experiment data and the generated experiment plan, wherein the analysis results are stored in the same directory as the generated experiment data and the generated experiment plan.

28. The method according to claim 27, further comprising steps:
(i) generating at least one hyperlink to the data files on the archive to access the data files via a computer network; and
(ii) storing at least one hyperlink on the computer,
wherein at least one hyperlink is automatically linked to the generated experiment data and the generated experiment plan, and wherein at least one hyperlink is stored in the same directory as the analysis results.

29. The method according to claim 22, wherein step (i) further comprises steps:
(a) determining a dilution of the reagent combination;
(b) calculating a volume of the reagent combination;
(c) calculating a volume of a sample population of cells; and
(d) determining a quantity of at least one fluorescent dye for use in creating a multimarker Hi-D stain set for flow cytometry or fluorescence microscopy.

30. The method according to claim 29, wherein at least one of steps (a), (b), (c), and (d) is performed by a computer.

31. The method according to claim 18, wherein the computer allows a user to rapidly design or modify the multimarker experiment data.

32. The method according to claim 18, wherein the multimarker experiment data includes a multimarker stain set that combines twelve or more reagents.

33. The method according to claim 18, wherein ranking step (c) comprises identifying at least one type of cell, segregating at least one type of cell from the population of cells, or both.

34. The method according to claim 33, wherein ranking step (c) is performed manually according to user generated preferences.

35. The method according to claim 33, wherein ranking step (c) is performed automatically according to a predetermined efficacy of the reagent combination with regard to at least one type of cell.

36. The method according to claim 18, further comprising steps:
(i) searching a data repository via a computer network to determine whether at least one ingredient for at least one of the reagent combinations is available from at least one supplier; and
(ii) ordering a quantity of the ingredient from the supplier.

37. The method according to claim 18, wherein a user can search the plurality of reagent combinations to find a particular reagent combination.

38. The method according to claim 18, wherein step (c) the best dye combination provides for a minimal an amount of correction needed due to overlap of fluorescent dyes.

39. A method implemented by a computing device for determining an effective spectrum matrix of a flow cytometer that comprises a plurality of detectors for fluorescence compensation from raw fluorescence measurements in multicolor flow cytometry comprising:
(a) estimating background autofluorescence by measuring autofluorescence of a set of unstained cells or reagent capture particles with each of the plurality of detectors of the flow cytometer,
(b) measuring fluorescence of a set of cells or particle samples labeled singly with each fluorochrome of a plurality of fluorochromes,
wherein each fluorochrome of the plurality of fluorochromes is assigned a primary detector of a flow cytometer, and
wherein fluorescence data is obtained from each assigned primary detector of each fluorochrome of the plurality of fluorochromes;
(c) analyzing the fluorescence data from each assigned primary detector of each fluorochrome of the plurality of fluorochromes of step (b) by estimating the mean and standard deviation of the autofluorescence from the unstained sample in (a) for each detector;
(d) for each single fluorochrome labeled sample and each detector, estimating the standard deviation of each event, by scaling errors with the estimates in (c) and initially setting background to zero, and fitting a line through the mean of the autofluorescence data for each detector,
(e) for each single fluorochrome labeled sample estimating background signal level from the autofluorescence data; improving the estimate of the standard deviation of each event on the primary detector plus the estimated background; again fitting a line; and estimating the photo electron sensitivity scaling using this median value and rescaling all errors to be chi squared distributed with one degree of freedom;
(f) for each detector, fitting a least squares line to the remaining data constrained to pass through the mean of the autofluorescence, wherein the slope of the line provides one coefficient in the effective spectrum matrix; and, fitting the model using a nonlinear least squares procedure, generating final estimates of background, photoelectron scaling, and overall quality of fit.

40. The method according to claim 39, step (a) further comprising obtaining autofluorescence data from each detector, and storing the data in a data storage device, wherein the mean and standard deviation of the autofluorescence data is measured by each detector by a computing device.

41. The method according to claim 39, step (c) further comprising (i) excluding any measurement of fluorescence wherein the fluorescence is within 10% of the maximum observable signal on any detector of the flow cytometer.

42. A method implemented by a computing device for selecting an optimal multimarker reagent combination for the identification and quantification of at least one molecule in or on at least one cell with or without reference to at least one property of at least one instrument-measurable atom or molecule associated with the reagent combination, the method comprising:
(a) specifying a plurality of markers to be detected by a plurality of reagents;
(b) specifying at least one measurable instrument comprising a plurality of detectors;
(c) generating a plurality of reagent combinations each comprising at least one of the plurality of reagents to detect the plurality of markers in (a),
(d) optimizing the reagent combinations by determining an effective spectrum matrix of the instrument comprising a plurality of detectors by
(1) estimating background autofluorescence by measuring autofluorescence of a set of unstained cells or reagent capture particles with each of the plurality of detectors of the flow cytometer,
(2) measuring fluorescence of a set of cells or particle samples labeled singly with each fluorochrome of a plurality of fluorochromes,
wherein each fluorochrome of the plurality of fluorochromes is assigned a primary detector of a flow cytometer, and
wherein fluorescence data is obtained from each assigned primary detector of each fluorochrome of the plurality of fluorochromes;
(3) analyzing the fluorescence data from each assigned primary detector of each fluorochrome of the plurality of fluorochromes of step (b) by estimating the mean and standard deviation of the autofluorescence from the unstained sample in (a) for each detector; and
(4) for each single fluorochrome labeled sample and each detector, estimating the standard deviation of each event by scaling errors with the estimates in (d), initially setting background to zero, and fitting a line through the mean of the autofluorescence data for each detector,
(5) for each single fluorochrome labeled sample, estimating background signal level from the autofluorescence data; improving the estimate of the standard deviation of each event on the primary detector plus the estimated background; again fitting a line; and estimating the photoelectron sensitivity scaling by resealing all errors to be chi squared distributed with one degree of freedom;
(6) for each detector, fitting a least squares line to the remaining data constrained to pass through the mean of the autofluorescence, wherein the slope of the line provides one coefficient in the effective spectrum matrix; and generating final estimates of background, photoelectron scaling, and overall quality of fit by a nonlinear least squares procedure; and
(d) ranking the reagent combinations according to at least one user defined or system defined criterion selected from the group consisting of spectral interactions, detectors on an instrument, illumination sources on an instrument, amount of reagent on-hand, known reactivities of reagents in each reagent combination; known cross-reactivities of reagents in each reagent combination, properties of each reagent in each reagent combination, available analysis capabilities, and species of an instrument;

and
(e) selecting the reagent combinations that fit within fluorescence spectral detection limitations of the instrument and within limitations imposed by treatment of the cells.

43. The method according to claim 42, wherein step (a) further comprises specifying at least one level of expression of one or more marker in the plurality of markers expected to be detected on or in each of a plurality of cells.

44. The method according to claim 42, wherein in step (c) the reagent combinations further comprise a list of available reagents and a list of needed reagents.

45. The method according to claim 44, wherein step (c) further comprises comparing the list of needed reagents against at least one data repository of at least one supplier.

46. The method according to claim 45, step (c) further comprising (ii) excluding any measurement of fluorescence recorded on the primary detector for the fluorochrome where the fluorescence recorded is less than two standard deviations above the mean of the autofluorescence data of step (a).

* * * * *

UNITED STATES PATENT AND TRADEMARK OFFICE
CERTIFICATE OF CORRECTION

| | |
|---|---|
| PATENT NO. | : 8,731,844 B2 |
| APPLICATION NO. | : 13/105570 |
| DATED | : May 20, 2014 |
| INVENTOR(S) | : Leonore A. Herzenberg et al. |

It is certified that error appears in the above-identified patent and that said Letters Patent is hereby corrected as shown below:

In the specification,
Column 1, line 21: "contract A1077395 awarded" should be changed to
-- contract AI077395 awarded --

Signed and Sealed this
Third Day of May, 2016

Michelle K. Lee
*Director of the United States Patent and Trademark Office*